US012590952B2

(12) United States Patent
Srinivasan

(10) Patent No.: US 12,590,952 B2
(45) Date of Patent: Mar. 31, 2026

(54) METHODS FOR PERFORMING MINIATURIZED DYNAMIC ASSAYS USING MICROFLUIDICS AND RELATED SYSTEMS

(71) Applicant: BIOBRIDGE GLOBAL, San Antonio, TX (US)

(72) Inventor: Anand Srinivasan, San Antonio, TX (US)

(73) Assignee: BIOBRIDGE GLOBAL, San Antonio, TX (US)

( * ) Notice: Subject to any disclaimer, the term of this patent is extended or adjusted under 35 U.S.C. 154(b) by 0 days.

(21) Appl. No.: 19/171,004

(22) Filed: Apr. 4, 2025

(65) Prior Publication Data

US 2025/0258160 A1 Aug. 14, 2025

Related U.S. Application Data

(63) Continuation of application No. PCT/US2023/086488, filed on Dec. 29, 2023, which is a continuation-in-part of application No. PCT/US2023/086294, filed on Dec. 28, 2023.

(51) Int. Cl.
| | |
|---|---|
| *G01N 33/50* | (2006.01) |
| *C12M 1/00* | (2006.01) |
| *C12M 1/34* | (2006.01) |
| *C12M 3/06* | (2006.01) |
| *C12N 5/09* | (2010.01) |
| *G01N 21/64* | (2006.01) |
| *G01N 33/58* | (2006.01) |

(52) U.S. Cl.
CPC ......... *G01N 33/5017* (2013.01); *C12M 23/16* (2013.01); *C12M 41/14* (2013.01); *C12M 41/36* (2013.01); *C12N 5/0694* (2013.01); *G01N 21/6428* (2013.01); *G01N 33/5011* (2013.01); *G01N 33/5047* (2013.01); *G01N 33/582* (2013.01); *G01N 2500/10* (2013.01)

(58) Field of Classification Search
CPC .......... G01N 33/5017; G01N 33/5011; G01N 33/5047; G01N 33/582
See application file for complete search history.

(56) References Cited

U.S. PATENT DOCUMENTS

| | | | |
|---|---|---|---|
| 5,424,209 | A | 6/1995 | Kearney |
| 6,008,010 | A | 12/1999 | Greenberger et al. |
| 6,121,042 | A | 9/2000 | Peterson et al. |
| 6,678,391 | B2 | 1/2004 | Yahiro |
| 7,725,267 | B2 | 5/2010 | Prabhakarpandian et al. |
| 7,867,752 | B1 | 1/2011 | Greenberger et al. |
| 7,906,323 | B2 | 3/2011 | Cannon et al. |
| 8,055,034 | B2 | 11/2011 | Dube et al. |
| 8,175,814 | B2 | 5/2012 | Prabhakarpandian et al. |
| 8,241,892 | B2 | 8/2012 | Greenberger et al. |
| 8,383,395 | B2 | 2/2013 | Hata et al. |
| 8,445,261 | B2 | 5/2013 | Greenberger et al. |
| 8,589,083 | B2 | 11/2013 | Prabhakarpandian et al. |
| 8,600,168 | B2 | 12/2013 | Dube et al. |
| 8,849,037 | B2 | 9/2014 | Dube et al. |
| 9,023,642 | B2 | 5/2015 | Kleis et al. |
| 9,206,384 | B2 | 12/2015 | Lee et al. |
| 9,249,443 | B2 | 2/2016 | Wheeler et al. |
| 9,428,723 | B2 | 8/2016 | Lee et al. |
| 9,569,566 | B2 | 2/2017 | Zamierowski et al. |
| 10,453,551 | B2 | 10/2019 | Thouppaurachchi et al. |
| 10,520,425 | B2 | 12/2019 | Bassi et al. |
| 10,745,660 | B2 | 8/2020 | Tovar et al. |
| 10,775,364 | B2 | 9/2020 | Prabhakarpandian et al. |
| 10,829,730 | B2 | 11/2020 | Shen et al. |
| 10,960,394 | B2 | 3/2021 | Wu et al. |
| 11,125,686 | B2 | 9/2021 | Shaked et al. |
| 11,327,004 | B2 | 5/2022 | Meldrum et al. |
| 11,327,285 | B2 | 5/2022 | Xiang et al. |
| 11,422,355 | B2 | 8/2022 | Jackson et al. |
| 11,427,851 | B2 | 8/2022 | Kreuger et al. |
| 11,436,945 | B2 | 9/2022 | Basu et al. |
| 11,561,178 | B2 | 1/2023 | Kannan et al. |
| 11,567,063 | B2 | 1/2023 | Silva et al. |
| 11,643,632 | B2 | 5/2023 | Corbera et al. |
| 2002/0146817 | A1 | 10/2002 | Cannon et al. |
| 2004/0202994 | A1 | 10/2004 | Timperman |
| 2005/0282268 | A1 | 12/2005 | Kagayama et al. |
| 2006/0006067 | A1 | 1/2006 | Unger |
| 2008/0274905 | A1 | 11/2008 | Greene |
| 2010/0099177 | A1 | 4/2010 | Yang et al. |
| 2010/0151571 | A1 | 6/2010 | Vukasinovic et al. |

(Continued)

OTHER PUBLICATIONS

Ibidi Cell Cultured Under Flow. Ibidi Application Guide. Cells in Focus Ibidi. pp. 1-15 (Jun. 2019).*
"Cell Culture and Preparation for Imaging", ibidi Application Guide, 2020, pp. 1-12.
"Cell Culture Under Flow", ibidi Application Guide, Jun. 2019, pp. 1-15.
"Immunofluorescence Assays", ibidi Application Guide, 2019, pp. 1-16.
"Instruction Manual: ibidi Gas Incubation System—Silver Line", ibidi Cells in Focus, v 1.0, 2022, pp. 1-44.
"Instruction Manual: ibidi Heating System Slide / Dish—Silver Line", ibidi Cells in Focus, v 1.0, 2022, pp. 1-40.

(Continued)

*Primary Examiner* — Gailene Gabel
(74) *Attorney, Agent, or Firm* — Norton Rose Fulbright US LLP

(57) ABSTRACT

Some methods of performing an assay comprise culturing target cells in one or more channels of one or more microfluidics chips, where each of the channel(s) can have a volume that is less than or equal to 100 microliters (μL). For each of one or more test liquids that each comprise a therapeutic reagent, the test liquid can flow over the cultured target cells in at least one of the channel(s) and, while the test liquid flows over the cultured target cells, data indicative of an interaction between the target cells over which the test liquid flows and the therapeutic reagent of the test liquid can be captured.

17 Claims, 29 Drawing Sheets

(56)             References Cited

U.S. PATENT DOCUMENTS

| | | | |
|---|---|---|---|
| 2010/0170796 | A1 | 7/2010 | Bhatia et al. |
| 2011/0081664 | A1 | 4/2011 | Forbes et al. |
| 2011/0183312 | A1 | 7/2011 | Huang et al. |
| 2012/0264134 | A1 | 10/2012 | Ionescu-Zanetti et al. |
| 2013/0143230 | A1 | 6/2013 | Tolias et al. |
| 2013/0261021 | A1 | 10/2013 | Bocchi et al. |
| 2013/0295551 | A1 | 11/2013 | Eddington et al. |
| 2014/0072955 | A1 | 3/2014 | Callahan et al. |
| 2014/0133732 | A1 | 5/2014 | Dube et al. |
| 2014/0255970 | A1 | 9/2014 | Prabhakarpandian et al. |
| 2015/0004637 | A1 | 1/2015 | Cohen et al. |
| 2016/0097028 | A1 | 4/2016 | Tung et al. |
| 2016/0161392 | A1 | 6/2016 | Ionescu-Zanetti et al. |
| 2016/0169801 | A1 | 6/2016 | Rogacs et al. |
| 2017/0138924 | A1 | 5/2017 | Beighley et al. |
| 2017/0248583 | A1* | 8/2017 | Simmons ............ C12N 5/0075 |
| 2018/0043357 | A1 | 2/2018 | Bocchi et al. |
| 2018/0185839 | A1 | 7/2018 | Jain et al. |
| 2018/0267021 | A1 | 9/2018 | Suresh et al. |
| 2018/0291417 | A1 | 10/2018 | Tipgunlakant et al. |
| 2018/0356397 | A1 | 12/2018 | Cho |
| 2019/0233791 | A1 | 8/2019 | Chung et al. |
| 2019/0283026 | A1 | 9/2019 | Loutherback et al. |
| 2020/0158717 | A1 | 5/2020 | Ben-Yakar et al. |
| 2020/0286580 | A1 | 9/2020 | Chait et al. |
| 2020/0318077 | A1 | 10/2020 | Nahmias et al. |
| 2020/0384471 | A1 | 12/2020 | Lin et al. |
| 2020/0400669 | A1* | 12/2020 | Chapman ........... G01N 33/5047 |
| 2021/0003554 | A1 | 1/2021 | Hickman et al. |
| 2021/0040433 | A1 | 2/2021 | Shen et al. |
| 2021/0054319 | A1 | 2/2021 | Levenberg et al. |
| 2021/0079337 | A1 | 3/2021 | Zenhausern et al. |
| 2021/0095235 | A1 | 4/2021 | Collins et al. |
| 2021/0139829 | A1 | 5/2021 | Griffith et al. |
| 2021/0278652 | A1 | 9/2021 | Donneys et al. |
| 2021/0292702 | A1 | 9/2021 | Miled et al. |
| 2021/0316302 | A1 | 10/2021 | Suh et al. |
| 2021/0341378 | A1 | 11/2021 | Jang et al. |
| 2021/0348096 | A1 | 11/2021 | Llamazares et al. |
| 2021/0354140 | A1 | 11/2021 | Gerber et al. |
| 2021/0394177 | A1 | 12/2021 | Jain et al. |
| 2021/0402399 | A1 | 12/2021 | Sharma et al. |
| 2021/0403847 | A1 | 12/2021 | Takayama et al. |
| 2021/0404937 | A1 | 12/2021 | Sarioglu et al. |
| 2022/0041967 | A1 | 2/2022 | Song et al. |
| 2022/0089989 | A1 | 3/2022 | Ingber et al. |
| 2022/0091404 | A1 | 3/2022 | Gatenholm et al. |
| 2022/0120660 | A1 | 4/2022 | Kikuchi et al. |
| 2022/0161255 | A1 | 5/2022 | Kurz et al. |
| 2022/0171332 | A1 | 6/2022 | Cuche et al. |
| 2022/0205914 | A1 | 6/2022 | Borja et al. |
| 2022/0236148 | A1 | 7/2022 | Cheung et al. |
| 2022/0243160 | A1 | 8/2022 | Lacombe et al. |
| 2022/0258160 | A1 | 8/2022 | Khoo et al. |
| 2022/0277571 | A1 | 9/2022 | Nakatomi et al. |
| 2022/0325240 | A1 | 10/2022 | McFarland et al. |
| 2022/0356429 | A1 | 11/2022 | Lowe, Jr. et al. |
| 2022/0380713 | A1 | 12/2022 | Wang et al. |
| 2023/0078827 | A1 | 3/2023 | Huh et al. |
| 2023/0080802 | A1 | 3/2023 | Nguyen et al. |
| 2023/0095664 | A1 | 3/2023 | Wagner |
| 2023/0116588 | A1 | 4/2023 | Sevenler et al. |
| 2023/0147702 | A1 | 5/2023 | Lee |
| 2023/0151333 | A1 | 5/2023 | Apostolou et al. |
| 2025/0216378 | A1* | 7/2025 | Srinivasan ......... G01N 33/5017 |

OTHER PUBLICATIONS

"Instruction Manual: ibidi Pump System", ibidi Cells in Focus, v 2.9, 2024, pp. 1-80.
"Instructions: μ-Slide I Luer", ibidi Cells in Focus, v 6.2, 2020, pp. 1-6.
"Microscopy With ibidi", ibidi Application Guide, 2021, pp. 1-28.
International Search Report issued in priority application No. PCT/US2023/086488, dated May 1, 2024.
International Search Report issued in priority application No. PCT/US2023/086294, dated Apr. 12, 2024.

* cited by examiner

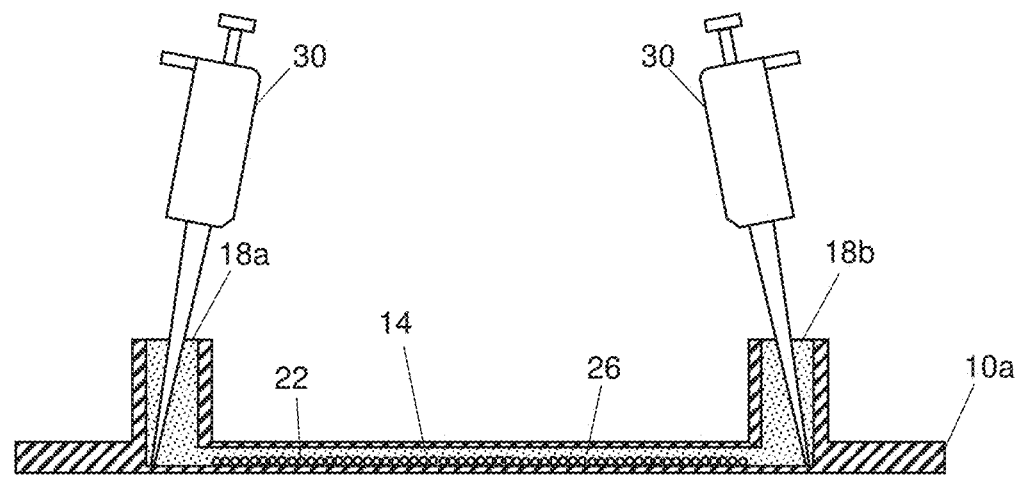
FIG. 6G
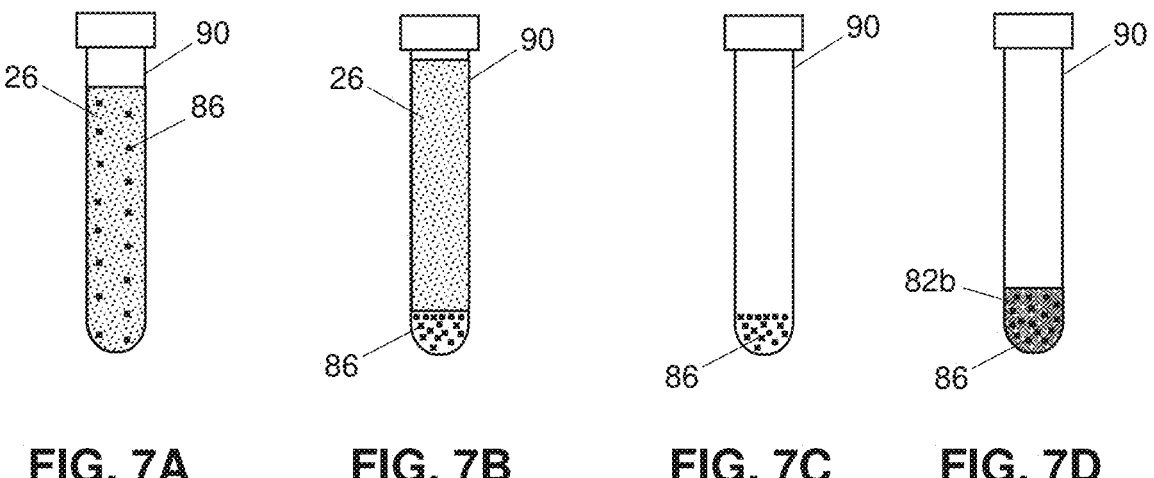
FIG. 7A      FIG. 7B      FIG. 7C      FIG. 7D

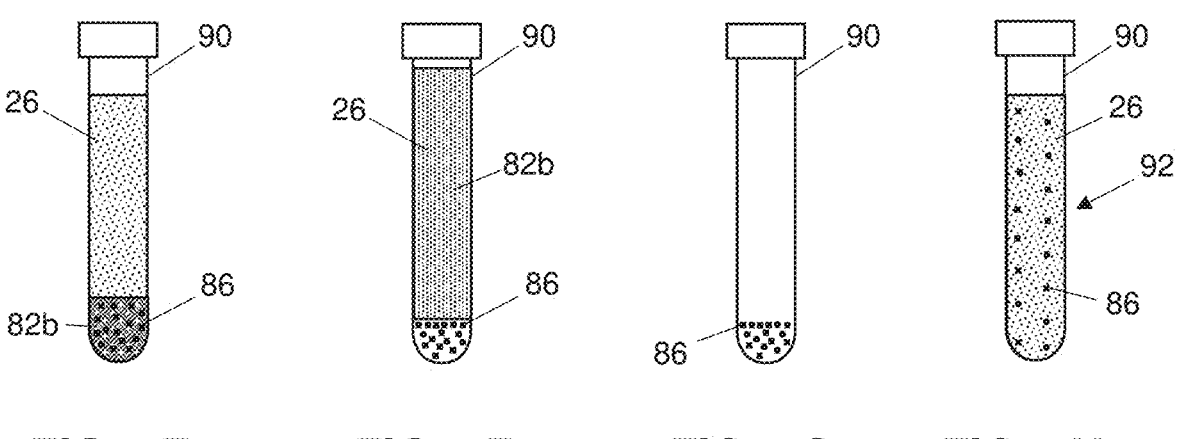
FIG. 7E      FIG. 7F      FIG. 7G      FIG. 7H

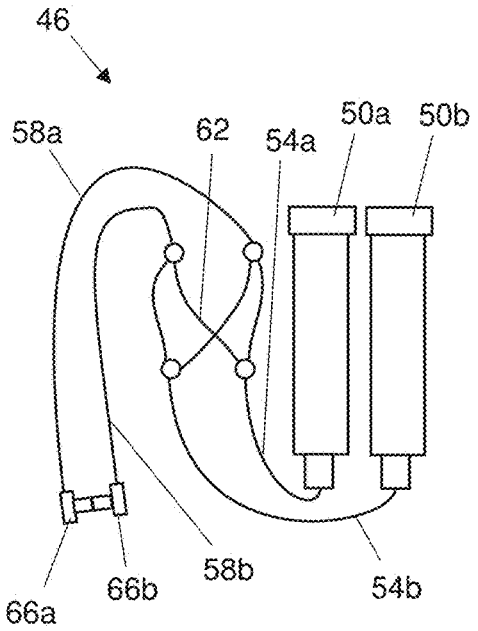
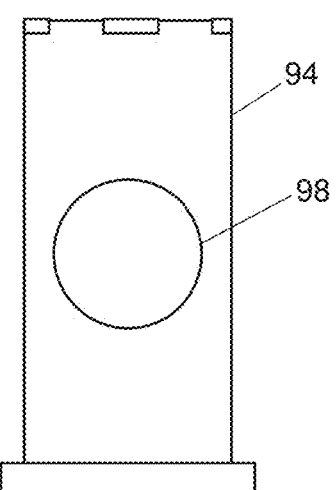
FIG. 8A
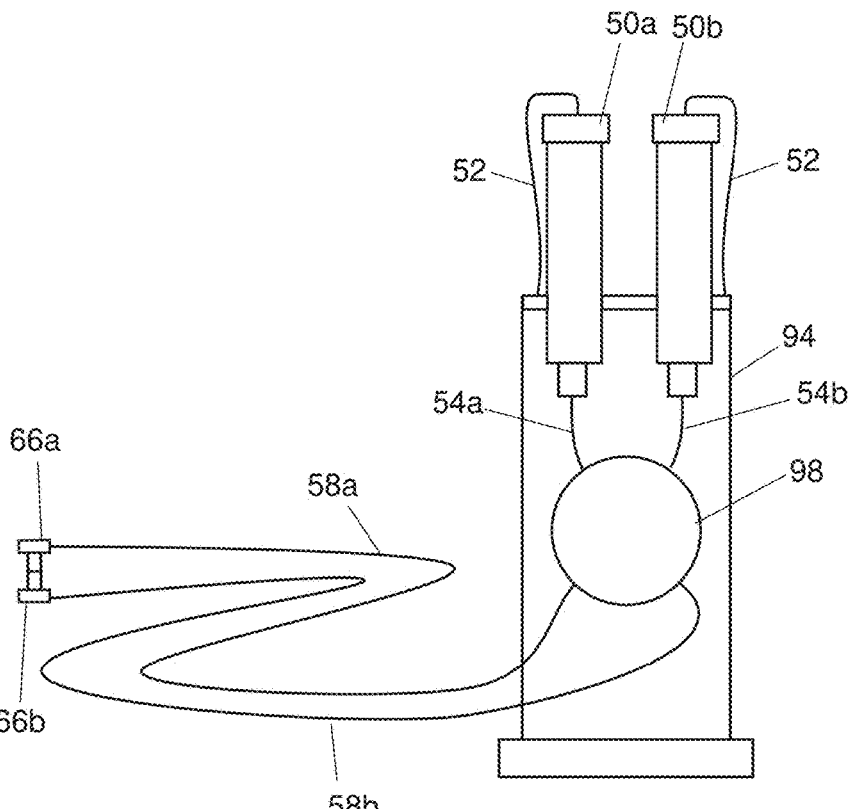
FIG. 8B

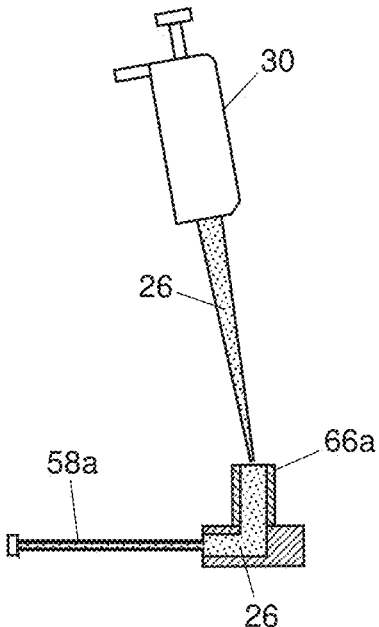
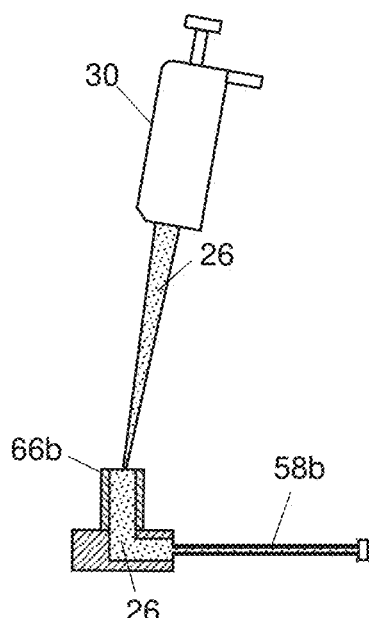
FIG. 9C
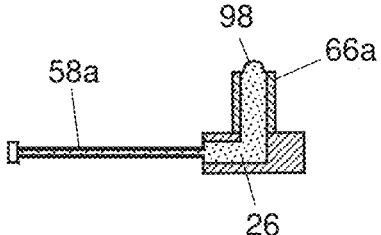
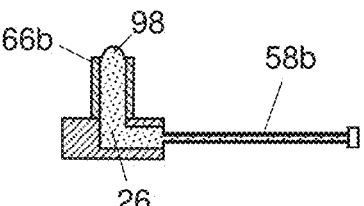
FIG. 9D

METHODS FOR PERFORMING MINIATURIZED DYNAMIC ASSAYS USING MICROFLUIDICS AND RELATED SYSTEMS

CROSS-REFERENCE TO RELATED APPLICATIONS

This application is a continuation of International Application No. PCT/US2023/086488, filed Dec. 29, 2023, which is a continuation-in-part of International Application No. PCT/US2023/086294, filed Dec. 28, 2023, the entire contents of each of which are incorporated into the present application in their entirety.

FIELD OF INVENTION

The present invention relates generally to miniaturized assays, which can be used to assess, by way of example and without limitation, advanced therapies.

BACKGROUND

Conventionally, biochemical and biological assays are conducted in petri dishes and well plates in which a target—such as cancer cells, pathogens, autoimmune cells, proteins, receptors, tissue, and/or the like—and a therapeutic reagent—such as a biologic, a small molecule drug, cells for immunotherapy, nucleic acids for gene therapies, and/or the like—are mixed and held together under static conditions to assess the effectiveness of the therapeutic reagent against the target. While such in vitro assays can be performed at a temperature representative of the physiological environment in which the therapeutic reagent is expected to be used, they otherwise may fail to fully mimic the conditions under which the therapeutic reagent would encounter and interact with the target in vivo. For example, a therapeutic reagent may have to flow to a target in the body, and the flow of fluid carrying the therapeutic reagent over the target may impact the therapeutic reagent's ability to achieve the desired interaction with the target (e.g., due to the mechanical forces experienced by the target, the related up/down regulation of nucleic acid responses, the time needed for the therapeutic reagent to bind to the target, and/or the like).

With these drawbacks, in vivo models are used to try to more-accurately represent how the therapeutic reagent may interact with a target under physiologically-relevant conditions. For example, to test the efficacy and/or safety of a therapeutic reagent for use by humans, the therapeutic reagent may first be tested in other animals such as mice, rats, apes, monkeys, and/or the like before testing the reagent in clinical trials involving humans. However, such animal models may still be a poor representation of how the therapeutic reagent will interact with the target in a human, especially for complex therapeutics such as cell and gene therapies (e.g., involving lymphocytes such as CAR T-cells to kill cancer or nucleic acids to manipulate gene expression) where the therapeutic reagent's interactions with the cells of other animals is unlikely to be the same as those with the cells of humans. For example, the potency and transduction effectiveness of a virus engineered to contain a nucleic acid and infiltrate a cell for gene therapy may vary between species.

SUMMARY

Accordingly, there is a need in the art for assays that can better mimic the physiologically-relevant conditions under which a therapeutic reagent will encounter and interact with a target in vivo to more accurately assess, for example, the efficacy and/or safety of the therapeutic reagent before the therapeutic reagent is administered to a subject. Methods and systems described herein can fulfill that need with a flow-based assay that employs one or more microfluidic chips to assess how one or more therapeutic reagents interact with target cells. Target cells can be cultured in one or more channels of the microfluidic chip(s), where the channel(s) each have a relatively small volume (e.g., less than or equal to 100 μL) to facilitate interactions between the therapeutic reagent(s) and target cells under physiologically-relevant conditions. For each of one or more test liquids that each comprise a therapeutic reagent, the test liquid can flow over the cultured target cells in at least one of the channel(s). Compared to conventional static in vitro assays, the flow of each test liquid containing the therapeutic reagent over the cultured target cells may better mimic the conditions that will exist in vivo (e.g., by mimicking the dynamic flow that occurs in, for example, blood circulation, the physiologically-relevant shear stress on the target, the physiologically-relevant flow rate of fluid over the target, and/or the like) such that the results of the assay are more representative of how the test liquid's therapeutic reagent will perform when administered to a subject. And the results of the flow-based assay may be more representative than those from in vivo models like animal studies because the cultured target cells can be from the species for which the therapeutic reagent is designed, especially when assessing cell and gene therapies—such as when the therapeutic reagent comprises lymphocytes (e.g., as a cancer treatment) or nucleic acids (e.g., for gene therapy)—where there can be large species-based differences in therapeutic efficacy. Fidelity to the conditions that will exist in vivo can be further maintained by, for example, heating the target cells and/or therapeutic reagent(s) and/or supplying a physiologically-relevant gas (e.g., comprising nitrogen ($N_2$), oxygen ($O_2$), carbon dioxide ($CO_2$), and/or compressed air) to a chamber in which the microfluidic chip(s) are disposed.

Some of the present methods of performing an assay comprise culturing target cells in one or more channels of one or more microfluidic chips, and some of the present systems comprise one or more microfluidic chips that each comprise one or more channels. Each of the channel(s), in some embodiments, has a volume that is less than or equal to 100 microliters (μL), optionally less than or equal to 50 μL. In some embodiments, each of the microfluidic chip(s) comprises one or more ports that are each in fluid communication with at least one of the channel(s) of the microfluidic chip. In some embodiments, the one or more channels of the one or more microfluidic chips comprise two or more channels. In some embodiments, the target cells include two or more types of target cells. In some of such embodiments where the one or more channels comprise two or more channels, culturing the target cells comprises culturing each type of the target cells in a respective one of the channels. In some methods, the target cells comprise cancer cells.

Some methods comprise, for each of one or more test liquids that each comprise a therapeutic reagent, flowing the test liquid over the cultured target cells in at least one of the channel(s). Some systems comprise a pump configured to be coupled to the port(s) of the microfluidic chip(s) and to pump one or more test liquids through the channel(s). In some methods, flowing the test liquid over the cultured target cells in at least one of the channel(s) is performed such that, for each of the channel(s), a shear stress between the test liquid and a surface in the channel is between 1 and 100 dynes per square centimeter (dyn/cm$^2$). Some methods comprise, for each of the test liquid(s), while flowing the test liquid over the cultured target cells, capturing data indicative of an interaction between the target cells over which the test liquid flows and the therapeutic reagent of the test liquid.

Some methods comprise, for each of the test liquid(s), while flowing the test liquid over the cultured target cells, heating the cultured target cells over which the test liquid flows. Some systems comprise a first incubator having a chamber configured to receive the microfluidic chip(s), the first incubator configured to heat the microfluidic chip(s) when the microfluidic chip(s) are disposed in the chamber. Some systems comprise a carbon dioxide ($CO_2$) source, an oxygen ($O_2$) source, a nitrogen ($N_2$) source, and/or an air source in which a pressure of the air is greater than ambient pressure are in fluid communication with the chamber of the first incubator. Some systems comprise a humidifier in fluid communication with the chamber of the first incubator. In some methods, for each of the test liquid(s), the microfluidic chip(s) comprising the channel(s) in which the test liquid flows are disposed in an incubator chamber while heating the cultured target cells and capturing data indicative of an interaction between the target cells and the therapeutic reagent of the test liquid. Some methods comprise, for each of the test liquid(s), directing carbon dioxide ($CO_2$) from a $CO_2$ source, oxygen ($O_2$) from an $O_2$ source, nitrogen ($N_2$) from an $N_2$ source, and/or air from an air source in which a pressure of the air is higher than ambient pressure into the incubator chamber while the microfluidic chip(s) comprising the channel(s) in which the test liquid flows are disposed in the incubator chamber and while flowing the test liquid over the cultured target cells. Some methods comprise, for each of the test liquid(s), directing moisture into the incubator chamber while the microfluidic chip(s) comprising the channel(s) in which the test liquid flows are disposed in the incubator chamber and while flowing the test liquid over the cultured target cells. For each of the test liquid(s), in some methods, flowing the test liquid over the cultured target cells is performed for at least 1 day.

For some methods in which the one or more channels of the microfluidic chip(s) comprise two or more channels, for each of the test liquid(s), flowing the test liquid over the target cells is performed such that the test liquid flows successively through at least two of the channels. In some methods where the one or more channels of the microfluidic chip(s) comprise two or more channels, the one or more test liquids comprise two or more test liquids. In some of such methods, for each of the test liquids, the therapeutic reagent of the test liquid is different than the therapeutic reagent of each other of the test liquids and the channel(s) through which the test liquid flows are different than the channel(s) through which each other of the test liquids flow.

In some methods, capturing data indicative of an interaction between the targets cells over which the test liquid flows and the therapeutic reagent of the test liquid comprises capturing one or more sequences of images. Some systems comprise one or more cameras. Each of the sequence(s) of images, in some methods, is of an area containing at least a portion of at least one of the channel(s) in which there are cultured target cells over which the test liquid flows. In some methods, each of the sequence(s) of images is captured with a respective one of one or more cameras. For each of the sequence(s) of images, in some methods, the camera captures at least 70 images of the sequence per second during at least a portion of a period over which the test liquid flows over the cultured target cells.

In some methods, the cultured target cells include a fluorescent agent having an emission spectrum that comprises a first peak wavelength. For each of the test liquid(s), in some of such methods, the therapeutic reagent includes a second fluorescent agent having an emission spectrum that comprises a second peak wavelength that is at least 10% different than the first peak wavelength. In some methods, for each of the sequence(s) of images, capturing the sequence of images comprises receiving light emitted by the first and/or second fluorescent agents at an image sensor of the camera that captures the sequence of images. In some methods, for each of the sequence(s) of images, receiving light emitted by the first and/or second fluorescent agents at the image sensor of the camera that captures the sequence of images comprises directing a first portion of the light emitted by the first and second fluorescent agents to a first part of the image sensor of the camera and a second portion of the light emitted by the first and second fluorescent agents to a second part of the image sensor of the camera. The first portion of light, in some methods, includes the first peak wavelength and does not include the second peak wavelength. The second portion of the light, in some methods, includes the second peak wavelength and does not include the first peak wavelength. Some methods comprise, for each of the sequence(s) of images, processing the captured sequence of images at least by, for each of the images of the sequence, superimposing a first portion of the image captured by the first part of the image sensor and a second portion of the image captured by the second part of the image sensor.

Some systems comprise first and second optical filters, wherein the first optical filter is transmissive over a first spectrum and the second optical filter is transmissive over a second spectrum that is different than the first spectrum. The first spectrum, in some systems, includes a wavelength of 525 nanometers (nm) and does not include a wavelength of 625 nm. In some systems, the second spectrum includes a wavelength of 625 nm and does not include a wavelength of 525 nm. Some systems comprise a microscope, and in some systems the microfluidic chip(s) and the first incubator are positionable relative to the camera(s) such that, for at least one of the channel(s), when the microfluidic chip(s) are disposed in the chamber of the first incubator and light is emitted from the channel and passes through the microscope, for at least one of the camera(s), a first portion of the light emitted from the channel that passes through the first filter strikes a first part of an image sensor of the camera and a second portion of the light emitted from the channel that passes through the second filter strikes a second part of the image sensor of the camera. In some systems where the one or more cameras comprise two or more cameras, the microfluidic chip(s) and the first incubator are positionable relative to the camera(s) such that, for at least one of the channel(s), when the microfluidic chip(s) are disposed in the chamber of the first incubator and light is emitted from the channel and passes through the microscope, a first portion of the light emitted from the channel that passes through the first filter strikes an image sensor of a first one of the cameras but not an image sensor of a second one of the cameras and a second portion of the light emitted from the channel that passes through the second filter strikes the image sensor of the second camera but not the image sensor of the first camera. In some embodiments, each of the camera(s) is a monochrome camera.

In some methods, the target cells are from a patient. Some of such methods comprise determining, for each of the test liquid(s) and based at least in part on the captured data, whether to administer the therapeutic reagent of the test liquid to the patient. Some methods comprise determining, for each of the test liquid(s) and based at least in part on the captured data, an extent to which the therapeutic reagent of the test liquid kills the target cells over which the test liquid flows and/or an extent to which the therapeutic reagent of the test liquid binds to the target cells over which the test liquid flows. In some methods, the therapeutic reagent comprises lymphocytes.

Some systems comprise a second incubator having a chamber that is larger than the chamber of the first incubator and is configured to receive the microfluidic chip(s), wherein the second incubator is configured to heat the microfluidic chip(s) when the microfluidic chip(s) are disposed in the chamber of the second incubator.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., two values being "substantially the same" includes those values being the same—as understood by a person of ordinary skill in the art. In any disclosed embodiment, the terms "substantially" and "about" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus or system that "comprises," "has," or "includes" one or more elements possesses those one or more elements but is not limited to possessing only those elements. Likewise, a method that "comprises," "has," or "includes" one or more steps possesses those one or more steps but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above in order to change the scope of a given claim from what it would otherwise be using the open-ended linking verb.

Further, an apparatus or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 6A-6G illustrate a process by which the cultured target cells in the channel of the microfluidic chip of FIG. 1A are stained such that they include a first fluorescent agent for imaging. In FIG. 6A a pipette is inserted into each of the ports of the microfluidic chip with the tip of the pipette facing away from the channel, and in FIG. 6B, for each of the ports, the pipette removes at least a portion of the growth medium in the port. In FIG. 6C a first staining solution comprising the first fluorescent agent is introduced into a first one of the ports and in FIG. 6D liquid is removed from a second one of the ports. In FIG. 6E a growth medium is introduced into the first port and in FIG. 6F liquid is removed from the second port. In FIG. 6G each of the ports is filled with growth medium.

FIGS. 7A-7H illustrate a process by which a therapeutic reagent is stained such that the therapeutic reagent includes a second fluorescent agent for imaging. In FIG. 7A, the therapeutic reagent is dispersed in a growth medium in a vial. In FIG. 7B, the growth medium and therapeutic reagent are segregated in the vial. In FIG. 7C, the growth medium is removed from the vial. In FIG. 7D, a second staining solution comprising the second fluorescent agent is introduced with the therapeutic reagent. For washing, in FIG. 7E growth medium is introduced into the vial with the therapeutic reagent and second staining solution, in FIG. 7F the therapeutic reagent is separated from a mixture of the second staining solution and growth medium, and in FIG. 7G the supernatant mixture is removed from the vial. After washing, in FIG. 7H growth medium is reintroduced into the vial holding the therapeutic reagent to resuspend the therapeutic reagent.

FIGS. 8A and 8B illustrate the coupling of the perfusion set in FIG. 5 to a fluidic unit.

FIGS. 9A-9G illustrates a process by which the perfusion set is placed in fluid communication with the channel of the microfluidic chip of FIG. 1A such that the pump can cause fluid to flow from the perfusion set and through the channel. In FIG. 9A growth medium is added to each of the ports and, as shown in FIG. 9B, this is performed such that the growth medium forms a convex meniscus protruding out of the port. In FIG. 9C, growth medium is added to the outlets of port connectors such that, as shown in FIG. 9D, a convex meniscus protruding out of each of the port connectors is formed. In FIGS. 9E and 9F the port connectors are each coupled to one of the ports of the microfluidic chips. FIG. 9G shows the perfusion set in fluid communication with the ports of the microfluidic chip.

FIG. 10 illustrates the coupled fluidic unit and perfusion set of FIGS. 8A and 8B, where the perfusion set is in fluid communication with two microfluidic chips that are arranged in series.

In FIG. 13, the stage-top incubator is in fluid communication with a gas source and is disposed on a microscope by which a camera can view the flow of the therapeutic reagent over the cultured target cells.

In FIG. 14A test liquid containing the therapeutic reagent enters the channel through a first end of the channel, in FIG. 14B the test liquid flows through the channel in a direction toward a second end of the channel, and in FIG. 14C the test liquid exits the channel through the channel's second end. In FIG. 14D, cancer cells are in the channel and anticancer agents kills at least a portion of the cancer cells and/or attaches to at least some of the cancer cells.

DETAILED DESCRIPTION

Figure 1A:
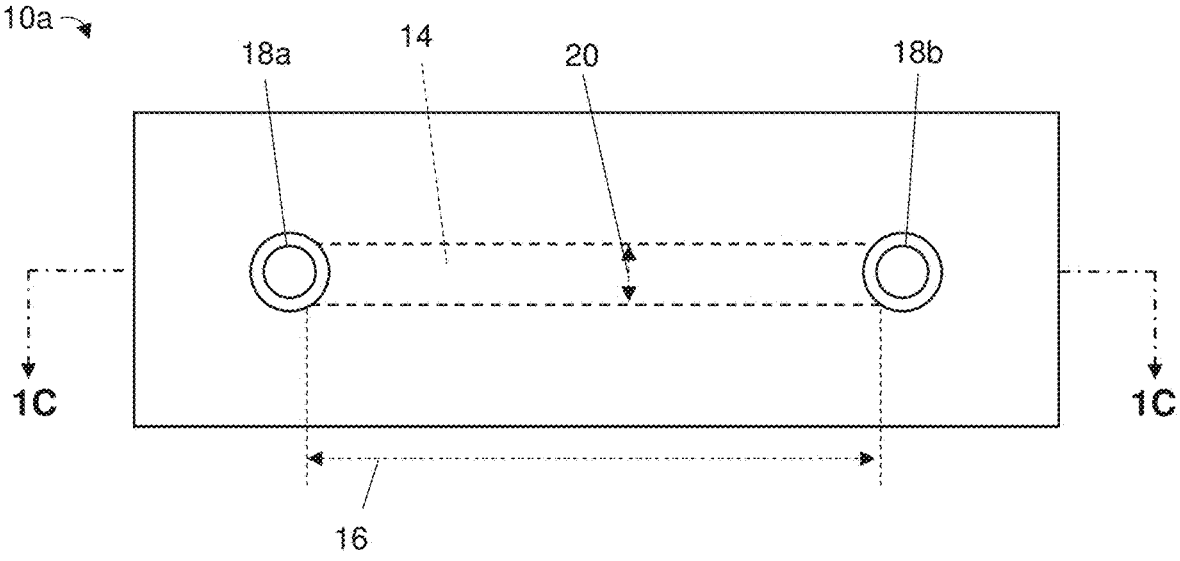
FIGS. 1A and 1B are top and side views, respectively, of a microfluidic chip of some of the present systems that has a single channel and is usable in some of the present methods of performing an assay.
Figure 1B:
Figure 1C:
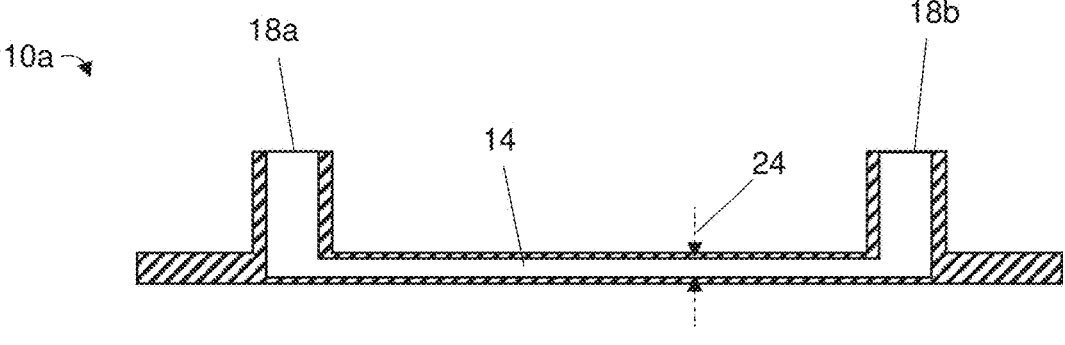
FIG. 1C is a sectional view of the chip of FIG. 1A taken along line 1C-1C of FIG. 1A.
Figure 2:
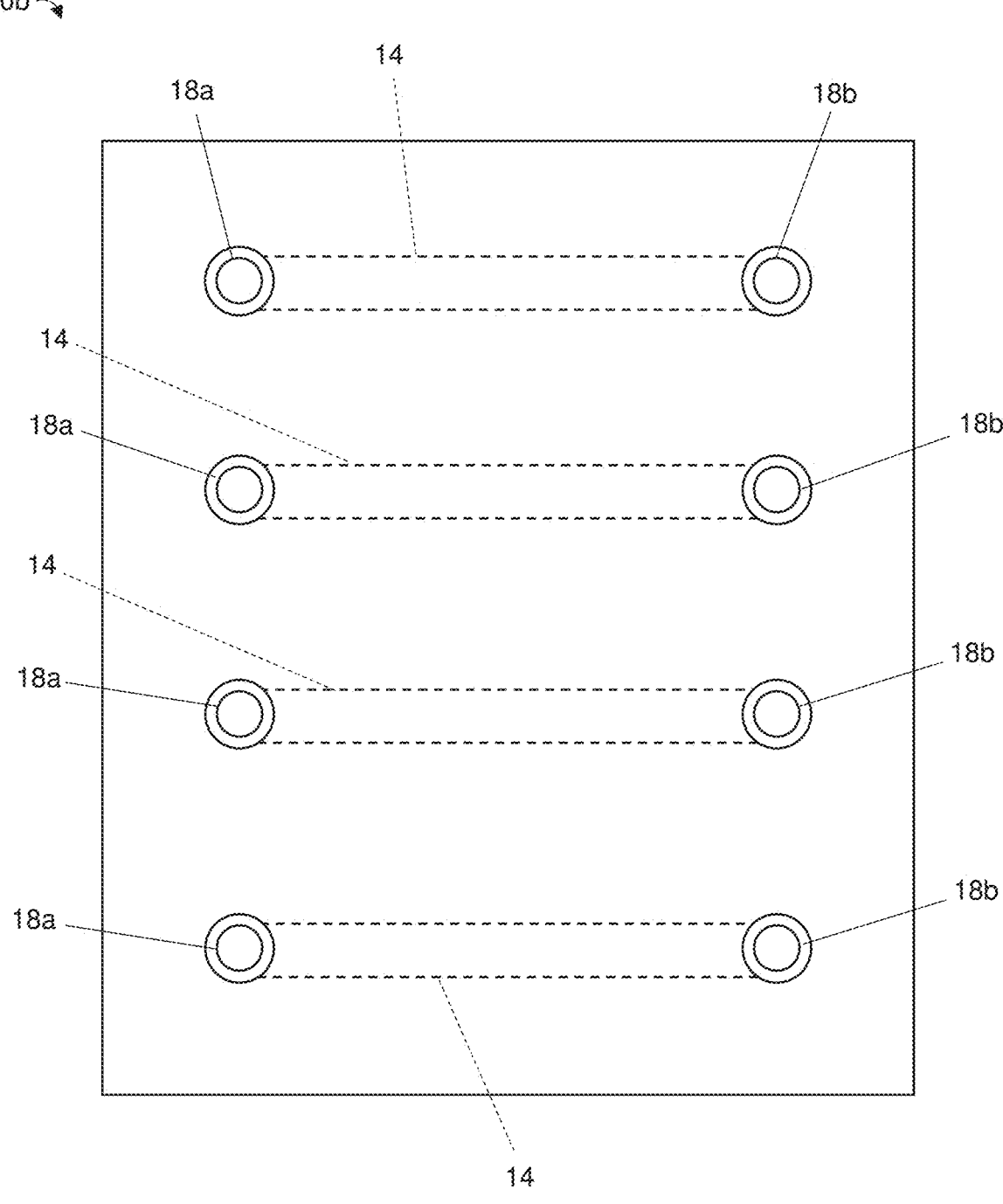
FIG. 2 is a top view of a microfluidic chip of some of the present systems that has multiple channels and is usable in some of the present methods of performing an assay.

Referring to FIGS. 1A-1C and 2, some of the present methods of performing an assay can employ, and some of the present systems can comprise, one or more microfluidic chips (e.g., 10a and 10b) that can each comprise a body (e.g., a polymeric body) defining one or more channels 14 in which the interaction between target cells and at least one therapeutic agent can be assessed. Each of channel(s) 14 can have a volume that is less than or equal to any one of, or between any two of, 100, 90, 80, 70, 60, 50, 40, 30, or 20 microliters (μL) (e.g., less than or equal to 50 μL, such as between 1.7 and 50 μL), such as with a length 16 that is less than or equal to any one of, or between any two of, 80, 75, 70, 65, 60, 55, 50, 45, 40, 35, 30, 25, or 20 millimeters (mm), a width 20 that is less than or equal to any one of, or between any two of, 8.0, 7.5, 7.0, 6.5, 6.0, 5.5, 5.0, 4.5, 4.0, 3.5, 3.0, 2.5, or 2.0 mm, and a height 24 that is less than or equal to any one of, or between any two of, 1.0, 0.9, 0.8, 0.7, 0.6, 0.5, 0.4, 0.3, 0.2, 0.15, or 0.10 mm. In some embodiments, each of channel(s) 14 can be sized to have a nano-liter-scale volume, such as a volume that is less than or equal to 100 nL. Such miniaturization can, in addition to reducing the amount of target cells and therapeutic reagent(s) needed for the assay, facilitate interactions between the target cells and therapeutic reagent(s) during the assay and accordingly reduce the time needed to perform the same.

As shown, chip 10a (FIGS. 1A-1C) comprises a single channel 14, which can be well-suited to assess the interaction between one set of target cells and one therapeutic reagent. However, as described in further detail below, multiple channels 14 can be employed—by using multiple ones of chips 10a and/or one or more chips 10b that each comprise a plurality of channels (FIG. 2)—to facilitate assays involving multiple types of cells and/or multiple therapeutic reagents.

Each of the microfluidic chip(s) can comprise one or more ports (e.g., 18*a* and 18*b*), where each of channel(s) 14 of the chip is in fluid communication with at least one of the port(s) such that target cells and a therapeutic reagent can be introduced into the channel. For example, as shown, each of the microfluidic chip(s) can comprise, for each of channel(s) 14 of the chip, first and second ports 18*a* and 18*b* that are each in fluid communication with and disposed at a respective one of the ends of the channel such that fluid can flow from the first port to the second port and/or from the second port to the first port through the channel.

Referring to FIGS. 3A-3E, some of the present methods comprise a step of culturing target cells (e.g., 22) in one or more of the channel(s) (e.g., 14) of the microfluidic chip(s) to increase the population of the target cells in the channel(s) for the assay, optionally such that the cultured target cells form spheroids and/or organoids (e.g., to mimic tissues, organs, tumors, and/or the like). The target cells can comprise any type of cells whose interaction with one or more therapeutic reagents—described in further detail below—is to be investigated, such as cancer cells (e.g., carcinoma, leukemia, lymphoma, myeloma, sarcoma, and/or mesothelioma cells), cells from one or more organs (e.g., from a pharynx, larynx, heart, artery, muscle, liver, gallbladder, kidney, bone, intestine, brain, lymph node, lung, spleen, stomach, vein, pancreas, bladder, skin, and/or the like), nerve cells, blood cells, and/or the like. A single type or two or more types of target cells can be cultured; for example, when there are multiple channels—whether of a single microfluidic chip or of multiple microfluidic chips—and multiple types of target cells, each type of the target cells can be cultured in a respective one of the channels to assess how the different types of target cells interact with the therapeutic reagent(s). Furthermore, the target cells can be from a human or a different type of animal (e.g., for veterinary, aquaculture, and/or the like medicine), and can be from a patient (e.g., for personalized medicine), a cell line (e.g., for a general therapeutic assessment), and/or the like.

In some embodiments, each of the channel(s) in which target cells are cultured can optionally be coated before introducing the target cells into the channel to facilitate attachment of the target cells, such as with serum, one or more recombinant proteins, cell and/or tissue lysates, and/or a hydrogel. For example, to coat with serum, serum can be introduced into the channel(s) of the microfluidic channel(s), the serum can be heated (e.g., in a chamber maintained at a temperature that is between 4 and 37° C.) while disposed in the channel(s), and the channel(s) can be washed. Such coating may be particularly beneficial when the target cells comprise, for example, cells from bone marrow, induced pluripotent stem cells (iPSCs), neural stem cells, cardiomyocytes, and/or the like, as such cells may not readily attach to a polymeric material of a microfluidic chip.

Figure 3A:
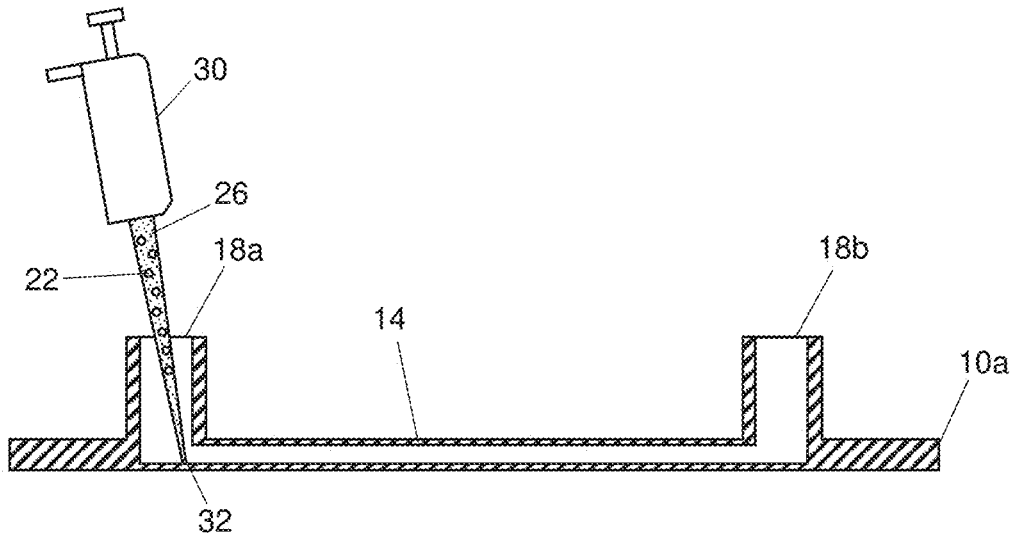
FIGS. 3A and 3B illustrate dispensing of target cells into the channel of the microfluidic chip of FIG. 1A for culturing.
Figure 3B:
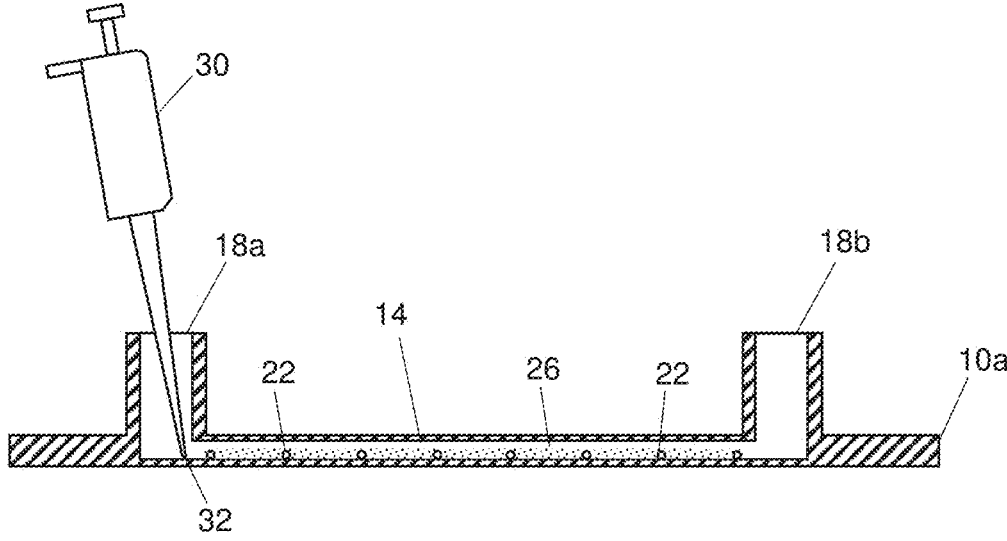
Figure 3C:
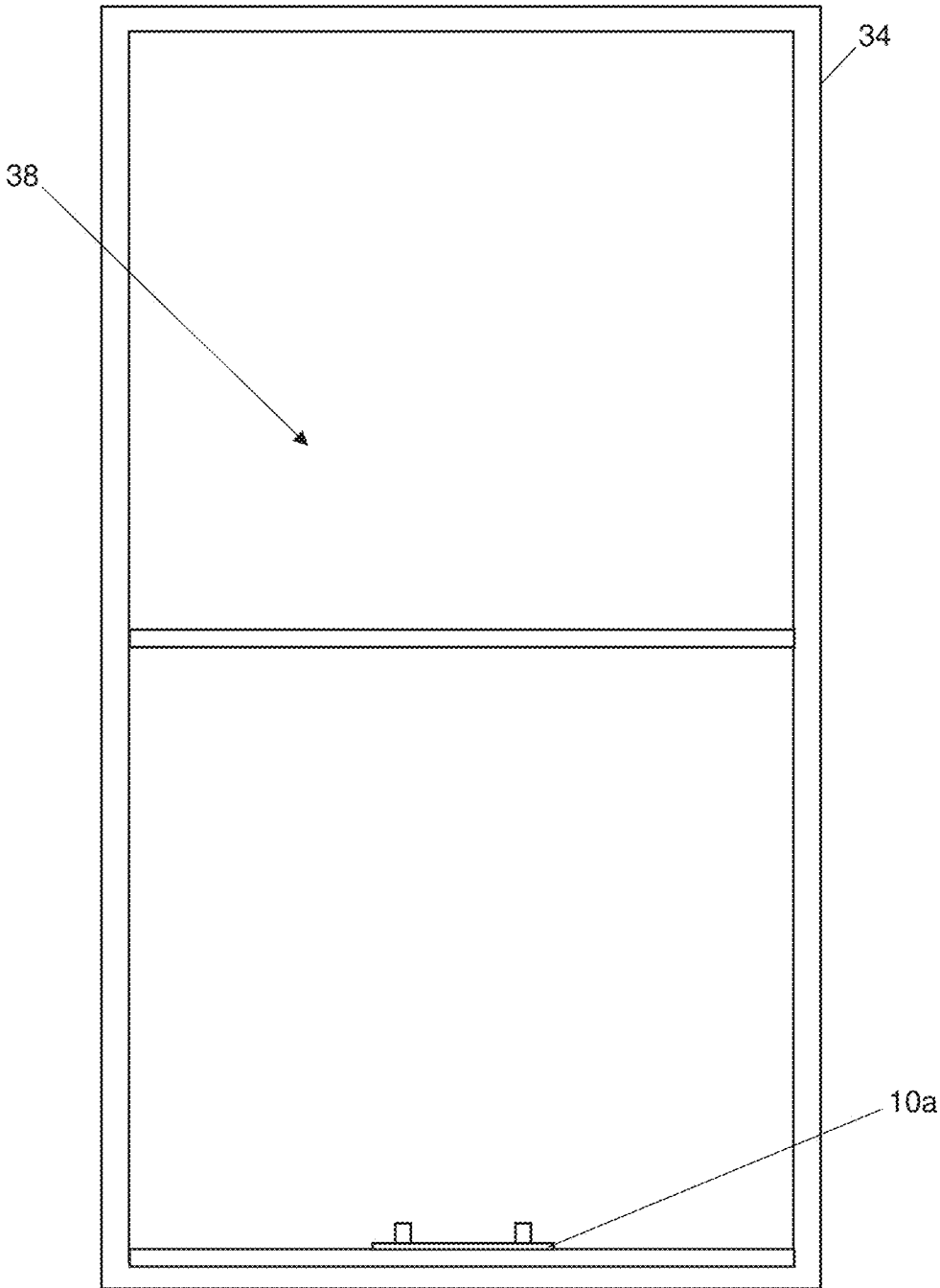
FIG. 3C illustrates an incubator of some of the present systems, where the microfluidic chip of FIG. 1A is disposed in the incubator to facilitate attachment of the target cells to the chip.

To culture the target cells, the target cells can be introduced into the channel(s) of the microfluidic chip(s) while the target cells are disposed in a growth medium (e.g., 26) (FIGS. 3A and 3B). The growth medium can comprise, for example, a nutrient broth comprising a carbon-containing compound (e.g., glucose), water, serum, one or more salts, one or more cell lysates, and/or one or more amino acids (existing alone or part of one or more proteins such as one or more recombinant proteins) to promote the proliferation of the target cells. A concentration of the target cells in the growth medium can be greater than or equal to any one of, or between any two of, 0.5, 0.75, 1.0, 1.25, 1.5, 1.75, 2.0, 2.25, 2.5, 2.75, or 3.0 million target cells per milliliter (mL) (e.g., at least 1.5 million target cells per mL), which can allow enough cell attachment and proliferation for the assay within a relatively short amount of time (e.g., in less than or equal to 24 hours). For each of the channel(s), the growth medium containing the target cells can be introduced into the channel via one of the port(s) that is in fluid communication with the channel, such as by inserting a pipette (e.g., 30) holding the growth medium and target cells into the port—preferably such that a tip (e.g., 32) of the pipette through which the growth medium and target cells are dispensed contacts an inlet of and faces the channel—and dispensing the growth medium and target cells out of the pipette such that they flow into the channel. Furthermore, for each of the channel(s), the volume of the growth medium containing target cells that is introduced into the channel is preferably less than the volume of the channel, such as less than or equal to any one of, or between any two of, 80%, 70%, 60%, 50%, 40%, or 30% (e.g., less than or equal to 50%) of the volume of the channel and/or less than or equal to any one of, or between any two of, 80, 70, 60, 50, 40, or 30 μL (e.g., less than or equal to 40 μL), which can facilitate culturing on the lower surface—rather than on the upper surface—of the channel such that the therapeutic reagent(s) can flow over the target cells as described in further detail below.

Figure 3D:
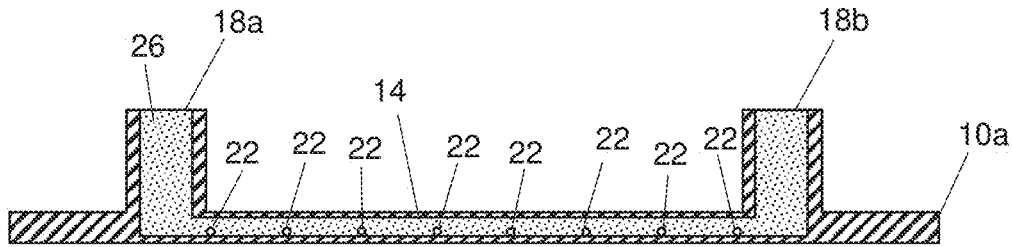
FIG. 3D illustrates dispensing of additional growth medium into the ports of the microfluidic chip of FIG. 1A after target cell attachment thereto.
Figure 3E:
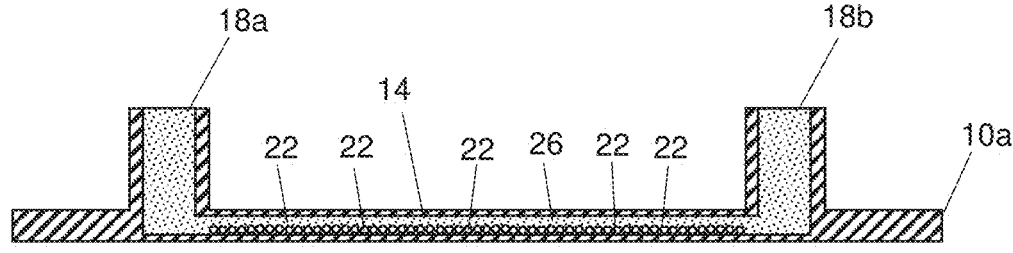
FIG. 3E illustrates the target cells in the channel of the microfluidic chip of FIG. 1A after culturing is complete.

Culturing the target cells can further comprise, after introducing the target cells into the channel(s), disposing the microfluidic chip(s) in a chamber (e.g., 38) of an incubator (e.g., 34) of some of the present systems (FIG. 3C) to facilitate attachment of the target cells to the lower surface of the channel and proliferation of the target cells. In the incubator, the target cells can be heated, such as by maintaining a temperature in the chamber of the incubator that is greater than or equal to any one of, or between any two of, 30, 31, 32, 33, 34, 35, 36, 37, 38, 39, or 40° C. (e.g., at least 35° C.) while the microfluidic chip(s) are disposed in the chamber. Furthermore, a culture-fostering environment can be promoted by placing the microfluidic chip(s) on a slide holder that comprises one or more—optionally two or more—wells that each contain a liquid like a phosphate-buffered saline solution or water such that the microfluidic chip(s) are disposed on the slide holder while in the chamber of the incubator. After greater than or equal to any one of, or between any two of, 7, 8, 9, 10, 11, or 12 hours—which can be sufficient time for target cell attachment to the lower surface of each of the channel(s)—additional growth media can be introduced into the channel(s) and/or port(s) to further promote target cell proliferation (FIG. 3D). For example, for each of the port(s), greater than or equal to any one of, or between any two of, 30, 35, 40, 45, 50, 55, 60, 65, or 70 μL (e.g., at least 50 μL) of growth medium can be introduced into the port (e.g., such that at least some of the additional growth medium enters the channel(s) in fluid communication with the port), which optionally can be substantially the same as the volume of the port. The microfluidic chip(s) can remain in the chamber of the incubator for additional time such that the target cells can proliferate (FIG. 3E), optionally such that the cultured target cells cover greater than or equal to any one of, or between any two of, 75%, 80%, 85%, 90%, or 95% (e.g., at least 95%) of the lower surface of each of the channel(s).

Figure 4:
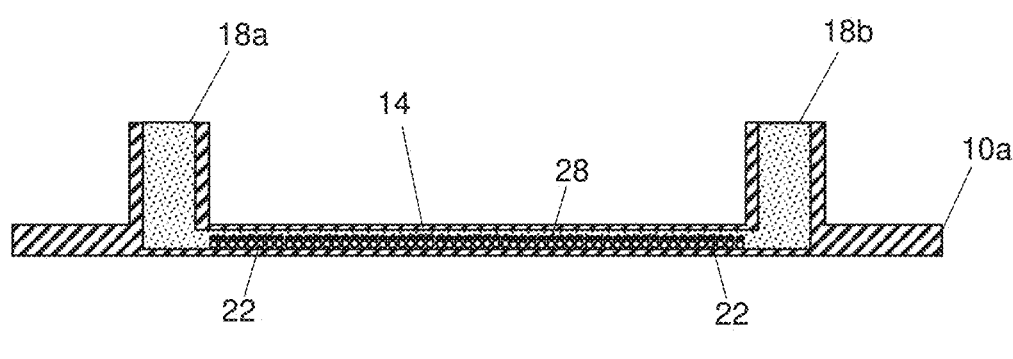
FIG. 4 illustrates a cell culture in the microfluidic chip of FIG. 1A in which a layer of cells of a different type than the target cells is disposed over the target cells in the channel.

In some embodiments, the cultured target cells can be arranged in the channel(s) in a manner that allows a characterization of how therapeutic reagent(s) permeate through one or more physiologically-relevant interfaces to reach the target cells. For example, for each of the channel(s) in which target cells are cultured, there can be a porous membrane dividing the channel into first and second portions, the target cells can be cultured in the first portion of the channel, and the second portion of the channel can be used for flowing a test liquid containing the therapeutic reagent as described in further detail below such that the therapeutic reagent has to pass through the membrane to reach the cultured target cells. Such an arrangement with a membrane may be well-suited to, for example, mimic the blood-brain barrier. Furthermore, while, as shown, culturing can be performed such that each of the channel(s) contains a single type of cells, referring to FIG. 4 in other embodiments multiple types of cells can be cultured in at least one of the channel(s). For example, one or more—optionally two or more—layers of overlying cells (e.g., 28) that are of a different type than the target cells (with—when there are multiple layers of overlying cells— each layer comprising cells of a different type than the cells of each other of the layers) can be cultured over the target cells. Such a multi-layered arrangement can represent inter-face(s) between tissues and/or organs such that the assay can be used to characterize how the therapeutic reagent(s) per-meate through the interface(s) to reach the target cells, such as for assays in which the therapeutic reagent comprises tumor infiltrating lymphocytes (TILS) that are designed to, in vivo, infiltrate the multi-layer environment of a tumor.

The cultured target cells can optionally be cryopreserved in the channel(s) of the microfluidic chip(s) such that they can be stored for later use. This can allow, for example, the mass production of microfluidic chips pre-populated with cultured target cells that can be readily used for assessing the interaction between the target cells and therapeutic reagent(s) at a later point in time without the need to spend time culturing additional target cells when the therapeutic reagent(s) are ready for the assessment.

Figure 5:
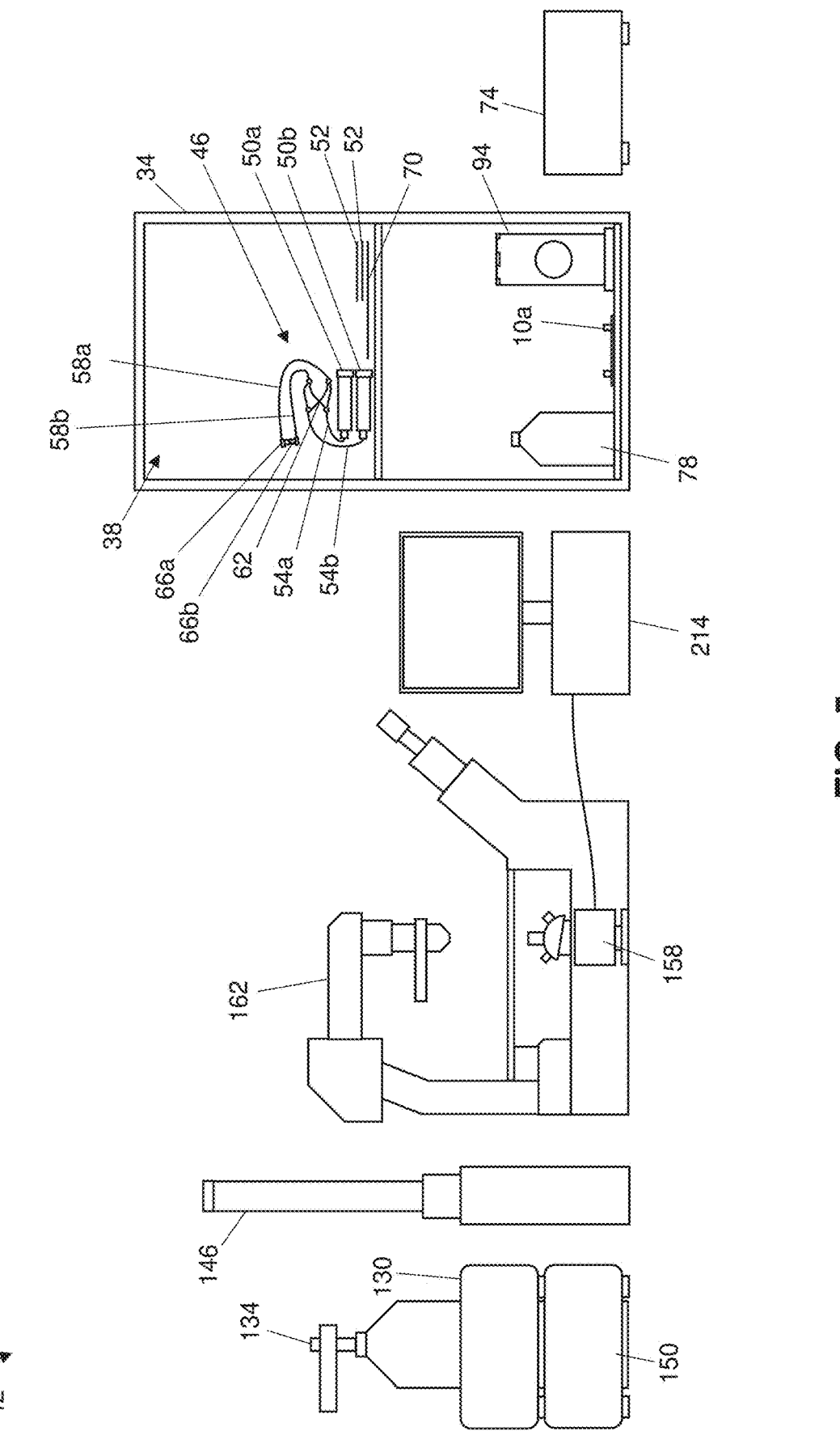
FIG. 5 is a front view of one of the present systems that is usable to perform some of the present methods of performing an assay, where growth media and a perfusion set and tubing used to flow a therapeutic reagent over the cultured target cells are disposed in the incubator of FIG. 3C.

Once the target cells are cultured in the channel(s) of the microfluidic chip(s), the interaction between the target cells and the therapeutic reagent(s) can be assessed. Referring to FIG. 5, shown is an embodiment 42 of the present systems that can be used for the assessment; while some of the present methods can be performed using system 42, system 42 is not limiting on those methods, which can be performed using any suitable system.

As shown, system 42 can comprise a pump 74 configured to be coupled to the port(s) of the microfluidic chip(s) such that the pump can pump one or more test liquids containing the therapeutic reagent(s) through the channel(s) of the microfluidic chip(s). As described in further detail below, such coupling can be achieved through at least one perfusion set 46 comprising one or more—optionally two or more—reservoirs 50a and 50b that can hold a test liquid, one or more tubes 54a, 54b, 58a, and 58b that are each in fluid communication with at least one of the reservoir(s), one or more port connectors 66a and 66b that can each be coupled to an end of one of the tube(s) and configured to be coupled to one of the port(s) of the microfluidic chip(s), and—when there are multiple tubes—one or more optional connections 62 between the tubes. When perfusion set 46's port connec-tor(s) 66a and 66b are coupled to one or more ports of the microfluidic chip(s), reservoir(s) 50a and 50b can be con-figured to be placed in fluid communication with the channel(s) of the microfluidic chip(s) that are in fluid communication with those port(s) via tube(s) 54a, 54b, 58a, and 58b and optional connection(s) 62, and pump 74 can be configured to be placed in fluid communication with the at least one of the reservoir(s) via a fluidic unit 94 that can be placed in fluid communication with reservoir(s) via one or more fluidic unit tube(s) 52 and with the pump via one or more pump tubes 70 such that the pump can drive liquid from at least one of the reservoir(s) to those channel(s) of the microfluidic chip(s).

Before flowing one or more test liquids over the cultured target cells, material that flows (e.g., growth medium) and equipment used for flow in the assessment (e.g., perfusion set 46, fluidic unit 94, fluidic unit tube(s) 52, and/or pump tube(s) 70) can be degassed to mitigate the risk of bubble formation, as bubbles might otherwise cause target cells to detach from the channel(s). Incubator 34 can be used to do so. For example, some methods comprise disposing the perfusion set (e.g., 46), fluidic unit (e.g., 94), fluidic unit tub(s) (e.g., 52), pump tube(s) (e.g., 70), and/or a container (e.g., 78) holding the growth medium in the chamber of the incubator and heating them, such as by maintaining a temperature in the chamber of the incubator that is greater than or equal to any one of, or between any two of, 30, 31, 32, 33, 34, 35, 36, 37, 38, 39, or 40° C. (e.g., at least 35° C.). Such heating can occur for greater than or equal to any one of, or between any two of, 7, 8, 9, 10, 11, or 12 hours.

Figure 6A:
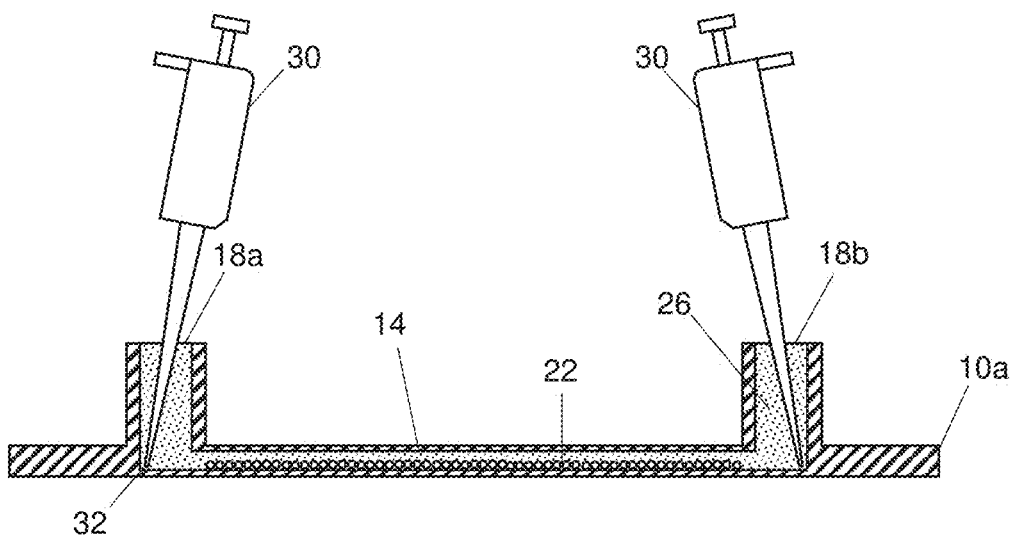
Figure 6B:
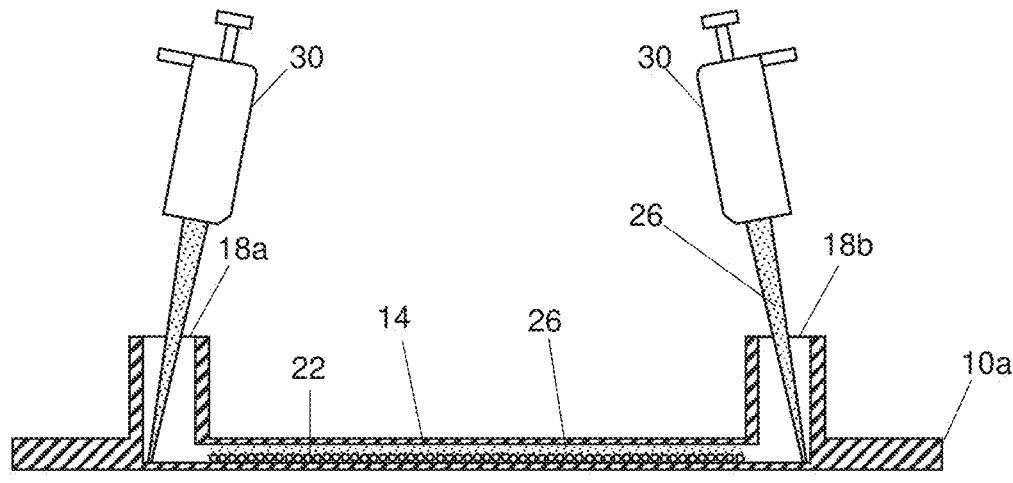
Figure 6C:
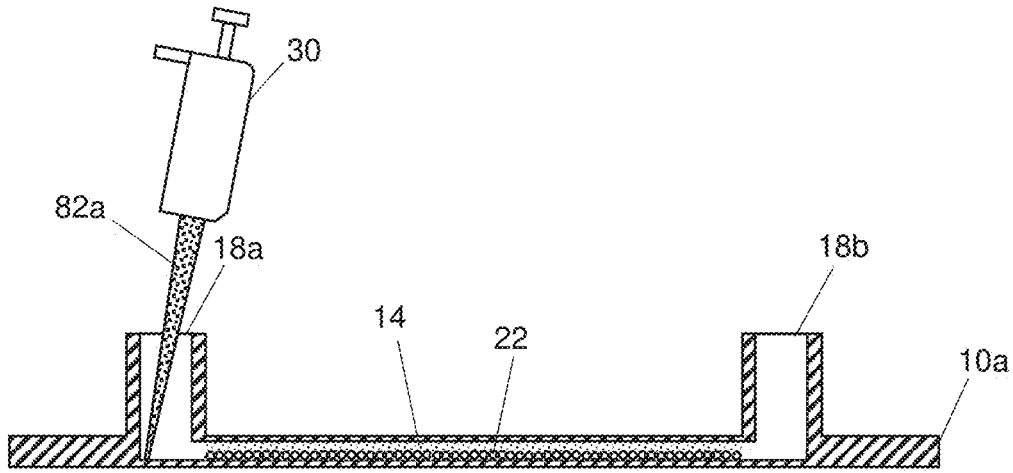
Figure 6D:
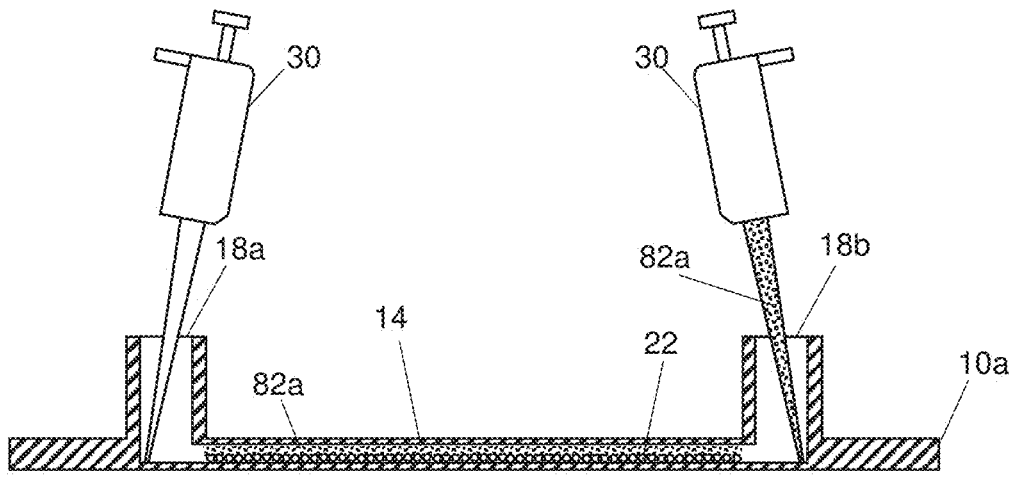
Figure 6E:
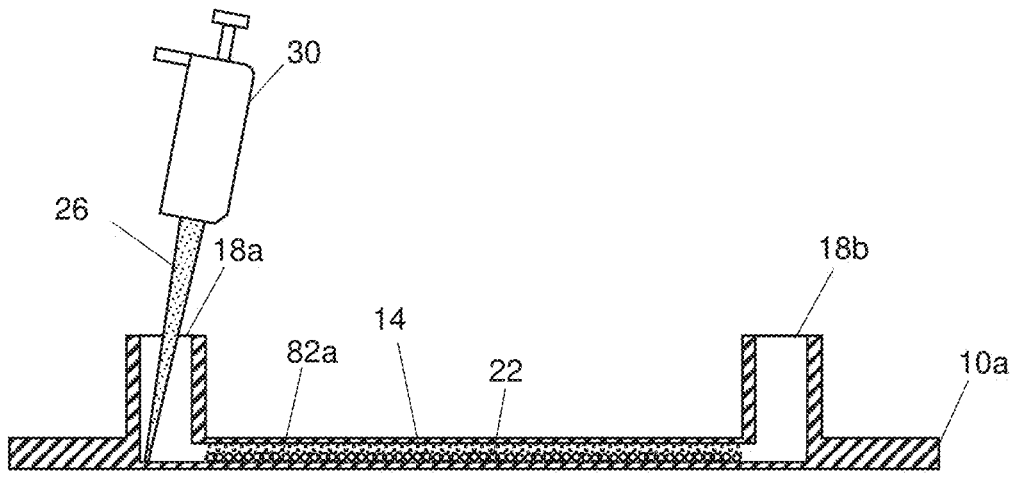
Figure 6F:
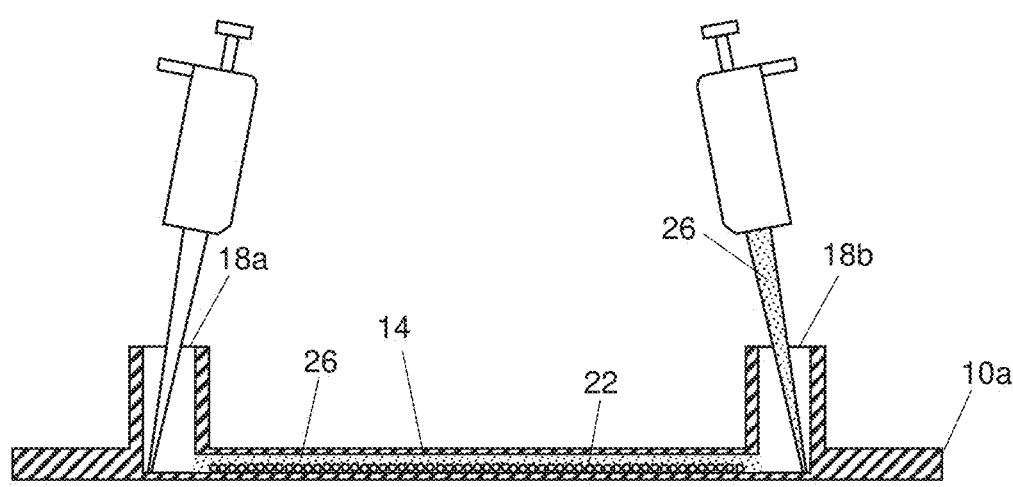

Furthermore, in some methods the cultured target cells and/or therapeutic reagent(s) can be stained before flowing the test liquid(s) over the cultured target cells to facilitate the assessment of the interactions therebetween. For example, referring to FIGS. 6A-6G, the cultured target cells can be stained such that they can be observed using fluorescence imaging. As shown, for each of the channel(s), at least a portion of the growth medium disposed in each of the port(s) that are in fluid communication with the channel can be removed from the port (FIGS. 6A and 6B), e.g., such that greater than or equal to any one of, or between any two of, 30, 35, 40, 45, 50, 55, 60, 65, or 70 μL (e.g., at least 50 μL) of growth medium is removed from each port. The removal can be performed using a pipette, preferably such that, for each of the channel(s), the tip of the pipette faces away from the channel while the pipette removes growth medium from each of the port(s) in fluid communication with the channel, which can mitigate the risk of disturbing the cultured target cells in the channel. Removing growth medium can allow room for the introduction of a staining solution.

After the removal of growth medium, a first staining solution (e.g., 82a) can be introduced into each of the channel(s) of the microfluidic chip(s) (FIGS. 6C and 6D), such as by introducing the first staining solution into at least one of the port(s) that are in fluid communication with the channel. For example, for each of the channel(s) having first and second ports that are each disposed at a respective one of the ends of the channel, the first staining solution can be introduced into the first port (e.g., using a pipette while the pipette's tip faces away from the channel) (FIG. 6C) and liquid can be removed from second port (e.g., also using a pipette while the pipette's tip faces away from the channel) (FIG. 6D), optionally such that the volume of liquid removed is substantially the same as the volume of the first staining solution introduced into the first port. The volume of the first staining solution introduced into the first port can be greater than or equal to any one of, or between any two of, 30, 35, 40, 45, 50, 55, 60, 65, or 70 μL (e.g., at least 50 μL). The introduction of the first staining solution into the first port and removal of liquid from the second port can be performed a plurality of times, such as three or more times, to ensure that substantially all of the growth medium in the channel is replaced with the first staining solution.

The first staining solution can comprise a first fluorescent agent that can comprise, for example, quantum dots, tagged peptides, tagged nucleic acids, and/or the like and can have an emission spectrum that comprises a first peak wave-length. As used herein, "an emission spectrum" can, but need not, consist of a single wavelength. An appropriate concentration of the first fluorescent agent in the first staining solution can depend on the type of fluorescent agent used; for example, when the first fluorescent agent comprises quantum dots, a concentration of the first fluorescent agent be greater than or equal to any one of, or between any two of, 5, 10, 15, 20, 25, 30, 35, 40, or 45 nanomoles per liter. And the first staining solution can comprise a phosphate buffer saline solution and/or growth medium (e.g., any of those described above) as a carrier. For example, the first staining solution can be made by combining the first fluorescent agent and a phosphate buffer saline solution, heating the resulting combination, and adding growth medium to the combination.

After the first staining solution is introduced into each of the channel(s) of the microfluidic chip(s), the cultured target cells and first staining solution in the channel(s) can be heated, such as by disposing the microfluidic chip(s) in the chamber of the incubator and maintaining a temperature in the chamber of the incubator that is greater than or equal to any one of, or between any two of, 30, 31, 32, 33, 34, 35, 36, 37, 38, 39, or 40° C. (e.g., at least 35° C.). Such heating can occur for greater than or equal to any one of, or between any two of, 0.5, 0.75, 1.0, 1.25, 1.5, 1.75, 2.0, or 2.25 hours (e.g., at least 1.5 hours). The heating can facilitate staining of the cultured target cells such that the cultured target cells include the first fluorescent agent.

After the cultured target cells are stained, the first staining solution can be removed from each of the channel(s) of the microfluidic chip(s) and growth medium (e.g., any of those described above) can be introduced therein (FIGS. 6E and 6F). For example, for each of the channel(s) having first and second ports that are each disposed at a respective one of the ends of the channel, the growth medium can be introduced into the first port (e.g., using a pipette while the pipette's tip faces away from the channel) (FIG. 6E) and liquid can be removed from second port (e.g., also using a pipette while the pipette's tip faces away from the channel) (FIG. 6F), optionally such that the volume of liquid removed is substantially the same as the volume of the growth medium introduced into the first port. The volume of growth medium introduced into the first port can be greater than or equal to any one of, or between any two of, 30, 35, 40, 45, 50, 55, 60, 65, or 70 µL (e.g., at least 50 µL). As with the introduction of the first staining solution, the introduction of the growth medium into the first port and removal of liquid from the second port can be performed a plurality of times, such as three or more times, to ensure that substantially all of the first staining solution in the channel is replaced with the growth medium. Each of the port(s) can optionally be filled with growth medium (FIG. 6G).

Referring to FIGS. 7A-7H, in some methods each of the therapeutic reagent(s) (e.g., 86) can be stained such that it can be observed using fluorescence imaging as well. For example, in the embodiment shown, at least one of the therapeutic reagent(s) can comprise lymphocytes such as T-cells, NK cells, and/or B cells that can be dispersed in a growth medium (e.g., any of those described above) (FIG. 7A), and for each of those therapeutic reagent(s) staining the therapeutic reagent can first comprise removing the growth medium by centrifuging a vial (e.g., 90) that contains the therapeutic reagent and growth medium to segregate them (FIG. 7B) such that the supernatant growth medium can be removed (FIG. 7C). With the growth medium removed, a second staining solution (e.g., 82b) can be introduced into the vial with the therapeutic reagent (FIG. 7D).

The second staining solution can comprise a second fluorescent agent that can comprise, for example, quantum dots, tagged peptides, tagged nucleic acids, and/or the like and can have an emission spectrum that comprises a second peak wavelength. The second peak wavelength can be different, such as at least 10%, 20%, 30%, or 40% different, than the first peak wavelength to allow differentiation between the cultured target cells and the therapeutic reagent during the assay. For example, the first peak wavelength can be less than or equal to any one of, or between any two of, 570, 545, 520, or 495 nm (e.g., between 495 and 570 nm, such as about 525 nm) and the second peak wavelength can be greater than or equal to any one of, or between any two of, 600, 625, 650, 675, 700, 725, or 750 nm (e.g., between 600 and 675 nm, such as about 625 nm), or vice versa. However, in other embodiments, any suitable first and second peak wavelengths can be employed to allow differentiation between the target cells and therapeutic reagent(s). An appropriate concentration of the second fluorescent agent in the second staining solution can, as with the first fluorescent agent, depend on the type of fluorescent agent used; for example, when the second fluorescent agent comprises quantum dots, a concentration of the second fluorescent agent can be greater than or equal to any one of, or between any two of, 5, 10, 15, 20, 25, 30, 35, 40, or 45 nanomoles per liter. And the second staining solution can comprise a phosphate buffer saline solution and/or growth medium (e.g., any of those described above) as a carrier. For example, the second staining solution can be made by combining the second fluorescent agent and a phosphate buffer saline solution, heating the resulting combination, and adding growth medium to the combination. Greater than or equal to any one of, or between any two of, 0.25, 0.5, 0.75, 1.0, 1.25, or 1.5 mL (e.g., at least 0.75 mL) of the staining solution can be introduced into the vial.

As with the staining of the cultured target cells, after the second staining solution is introduced into the vial holding the therapeutic reagent, the therapeutic reagent and the second staining solution in the vial can be heated to facilitate staining of the therapeutic reagent such that the therapeutic reagent comprises the second fluorescent agent, such as by disposing the vial in the chamber of the incubator and maintaining a temperature in the chamber of the incubator that is greater than or equal to any one of, or between any two of, 30, 31, 32, 33, 34, 35, 36, 37, 38, 39, or 40° C. (e.g., at least 35° C.). Such heating can occur for greater than or equal to any one of, or between any two of, 0.5, 0.75, 1.0, 1.25, 1.5, 1.75, 2.0, or 2.25 hours (e.g., at least 0.75 hours).

After the therapeutic reagent is stained, the second staining solution can be removed from the vial and growth medium (e.g., any of those described above) can be introduced into the vial to resuspend the therapeutic reagent (e.g., lymphocytes) in the growth medium. For example, one or more—optionally two or more—growth medium washes can be performed, where for each of the wash(es) greater than or equal to any one of, or between any two of, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mL of the growth medium can be introduced into vial (FIG. 7E), the vial can be centrifuged to separate the therapeutic reagent from a mixture of the second staining solution and growth medium (FIG. 7F), and the supernatant mixture can be removed from the vial (FIG. 7G). When there are multiple growth medium washes, in a first one of the washes the volume of growth medium introduced into the vial can be greater than the volume of growth medium introduced into the vial in a second one of the washes, such as with at least 7 mL introduced in the first wash and less than or equal to 4 mL introduced in the second wash. After the wash(es), the growth medium can be introduced into the vial holding the therapeutic reagent to resuspend the therapeutic reagent in growth medium (FIG. 7H), such as by introducing greater than or equal to any one of, or between any two of, 5, 6, 7, 8, 9, 10, or 11 mL (e.g., at least 7 mL) of growth medium into the vial. The resulting liquid can be one of the test liquid(s) (e.g., 92) used in the assay.

Referring to FIGS. 8A-8D and 9A-9G, with the test liquid(s) prepared for the assay, the connection(s) between the pump and microfluidic chip(s) that are required for the pump to pump the test liquid(s) through the channel(s) of the microfluidic chip(s) can be made. This can comprise coupling the above-described perfusion set(s) to a fluidic unit (e.g., 94) (FIGS. 8A and 8B) such that each of the perfusion set's reservoir(s)—which can have a capacity to hold sufficient liquid for the assay, such as at least 5, 6, 7, 8, 9, 10, 11, or 12 mL (e.g., at least 7 mL)—are in fluid communication with the fluidic unit (e.g., via one or more fluidic unit tubes 52). As shown, each perfusion set 46 can comprise first and second reservoirs 50a and 50b that are each coupled to and in fluid communication with a respective one of first and second reservoir tubes 54a and 54b, as well as first and second outlet tubes 58a and 58b that can each have an end coupled to a respective one of first and second port connectors 66a and 66b that are each configured to be coupled to a port of the microfluidic chip(s). A tube connection 62 can couple outlet tubes 58a and 58b to reservoir tubes 54a and 54b such that each of the outlet tubes is in fluid communication with each of the reservoir tubes. When perfusion set 46 is coupled to fluidic unit 94, tube connection 62 can be coupled to a valve 98 of the fluidic unit.

At least by manipulating the fluid communication that tube connection 62 creates between outlet tubes 58a and 58b and reservoir tubes 54a and 54b, fluidic unit 94 and its valve 98 can be configured to control the type of flow (e.g., unidirectional, pulsatile, or oscillatory) dispensed out of perfusion set 46, including which of outlet tubes 58a and 58b dispenses liquid and which of the outlet tubes receives liquid at a given point in time. For example, valve 98 can be movable between a (1) first state in which first outlet tube 58a is in fluid communication with first reservoir tube 54a but not with second reservoir tube 54b and second outlet tube 58b is in fluid communication with the second reservoir tube but not with the first reservoir tube, and (2) a second state in which the first outlet tube is in fluid communication with the second reservoir tube but not with the first reservoir tube and the second outlet tube is in fluid communication with the first reservoir tube but not with the second reservoir tube. To dispense liquid through first outlet tube 58a and return liquid through second outlet tube 58b, valve 98 can be moved to the first state when liquid is dispensed from first reservoir 50a (e.g., with liquid returning to second reservoir 50b) and to the second state when liquid is dispensed from the second reservoir (e.g., with liquid returning to the first reservoir). And to dispense liquid through second outlet tube 58b and return liquid through first outlet tube 58a, valve 98 can be moved to the first state when liquid is dispensed from second reservoir 50b (e.g., with liquid returning to first reservoir 50a) and to the second state when liquid is dispensed from the first reservoir (e.g., with liquid returning to the second reservoir).

For unidirectional flow, valve 98 can maintain the dispensing of liquid through one of outlet tubes 58a and 58b and the return of liquid through the other of the outlet tubes, while for oscillatory flow the valve can cause the dispensing of liquid to alternate between the outlet tubes. And, for pulsatile flow, valve 98 can intermittently stop the dispensing of liquid through any of outlet tubes 58a and 58b.

Figure 8C:
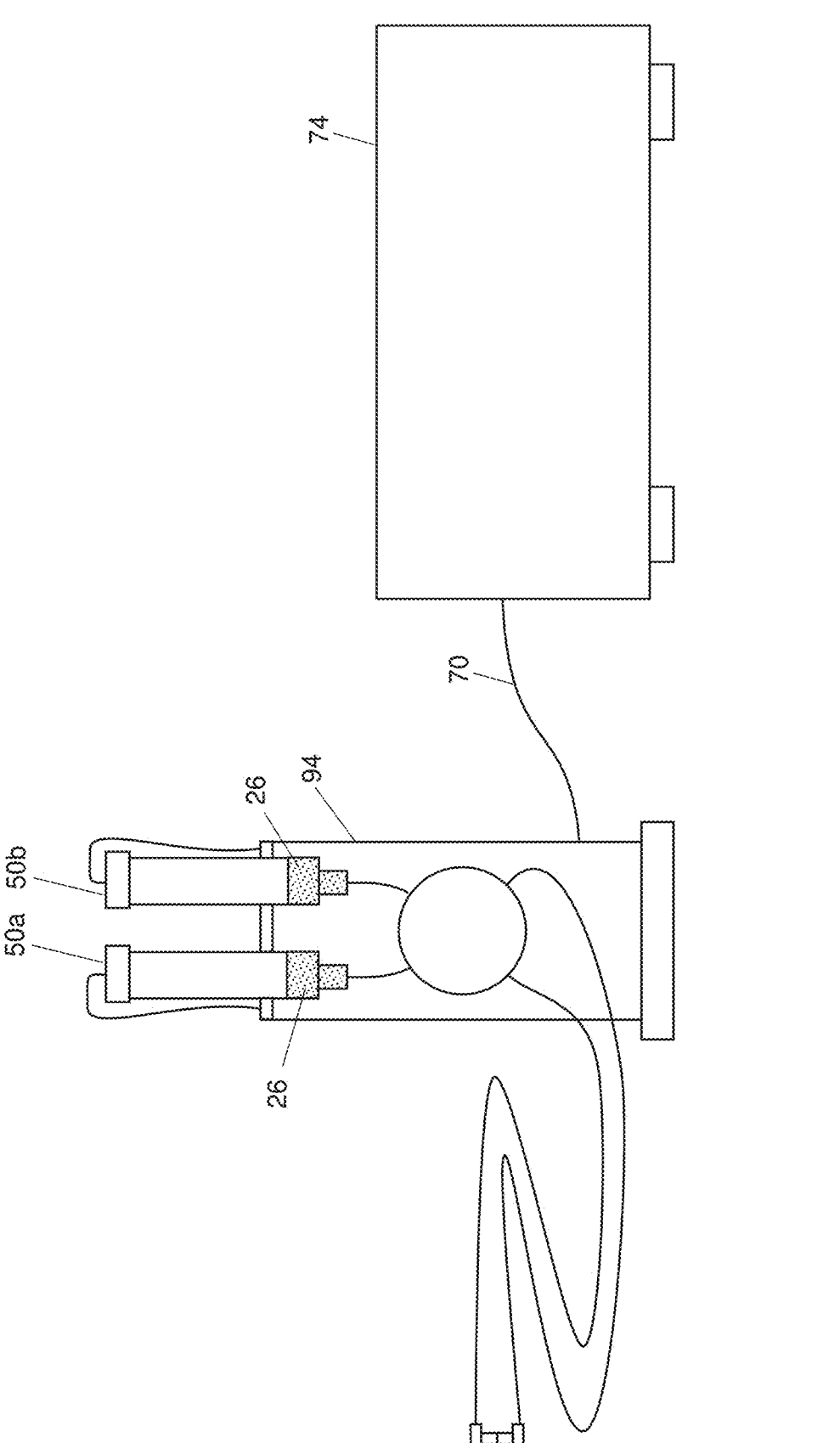
FIG. 8C illustrates the coupling of the fluidic unit of FIGS. 8A and 8B to a pump such that the pump is configured to pump fluid held in the perfusion set that is coupled to the fluidic unit.
Figure 8D:
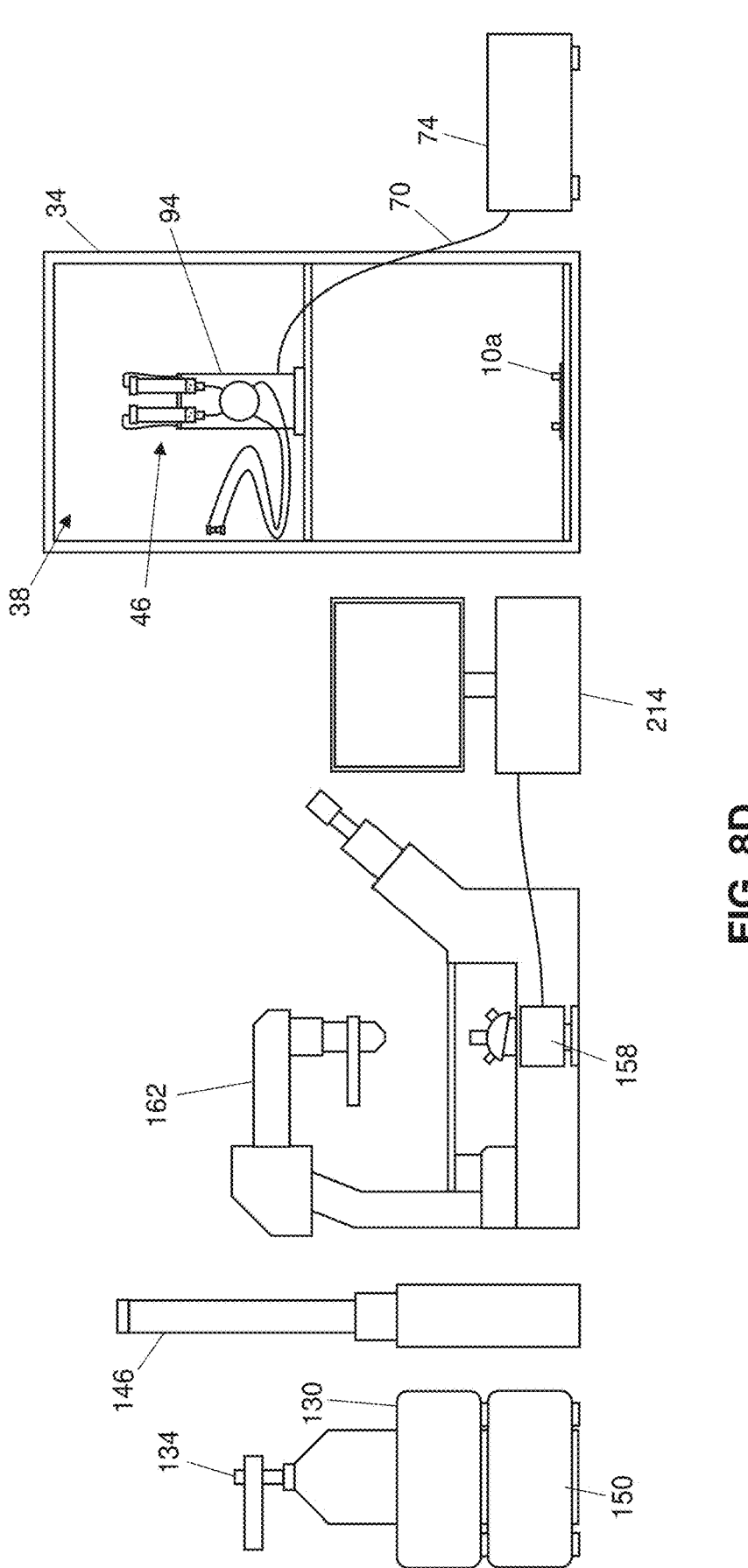
FIG. 8D illustrates the coupled fluidic unit and perfusion set of FIGS. 8A and 8B disposed in the incubator of the system of FIG. 5, where the pump of FIG. 8C is coupled to the fluidic unit.

To generate the pressure differential required to dispense liquid from perfusion set 46, fluidic unit 94 can be coupled to pump 74 via one or more pump tubes 70 such that the pump is in fluid communication with the fluidic unit and thus configured to be placed in fluid communication, via fluidic unit tube(s) 52, with at least one of reservoirs 50a and 50b of each of the perfusion set(s) (FIG. 8C). Pump 74 can, for example, increase pressure in one of reservoirs 50a and 50b and/or decrease pressure in the other of the reservoirs to cause liquid to be dispensed from one of the reservoirs and flow to the other of the reservoirs. As an illustration, to increase pressure in one of reservoirs 50a and 50b, pump 74 can be configured to pump an inert gas such as nitrogen ($N_2$) into the reservoir.

While as shown pump 74 is configured to pump liquid via a fluidic unit 94 and a single perfusion set 46 having two reservoirs 50a and 50b, two reservoir tubes 54a and 54b, two outlet tubes 58a and 58b, and two port connectors 66a and 66b, in other embodiments the pump can be configured to pump liquid in any suitable manner, including via multiple perfusion sets and/or at least one perfusion set having a different number of reservoirs, reservoir tubes, outlet tubes, and/or connectors (e.g., depending on how many microfluidic chip(s), channel(s), and/or port(s) are involved in the assay).

To further mitigate the risk of bubble formation, some methods comprise, for each perfusion set, after coupling the perfusion set to the fluidic unit (e.g., 94) and the fluidic unit to the pump, introducing growth medium (e.g., any of those described above) into each of the reservoir(s) of the perfusion set (FIG. 8C), such as greater than or equal or to any one of, or between any two of, 6, 7, 8, 9, 10, 11, 12, 13, or 14 mL (e.g., at least 10 mL) of growth medium, and dispensing the growth medium out of at least one of the reservoir(s) using the pump for degassing. For example, with the above-described perfusion set having two reservoirs and two port connectors, the port connectors can be coupled together such that growth medium dispensed through the first outlet tube (e.g., 58a) can return through the second outlet tube (e.g., 58b) and vice versa. For each of the reservoir(s) from which growth medium is dispensed, the pump can increase pressure in the reservoir by greater than or equal to any one of, or between any two of, 30, 35, 40, 45, 50, 55, or 60 mbar (e.g., at least 40 mbar) during the degassing. Furthermore, the perfusion set can be heated while dispensing the growth medium out of at least one of the reservoir(s), such as by disposing the perfusion set and the fluidic unit coupled thereto in the chamber of the incubator and maintaining a temperature in the chamber of the incubator that is greater than or equal to any one of, or between any two of, 30, 31, 32, 33, 34, 35, 36, 37, 38, 39, or 40° C. (e.g., at least 35° C.) (FIG. 8D), which can facilitate degassing. Dispensing the growth medium out of at least one of the reservoir(s) and heating the growth medium can be performed for greater than or equal to any one of, or between any two of, 15, 20, 25, 30, 35, or 40 minutes (e.g., at least 20 minutes).

Figure 9A:
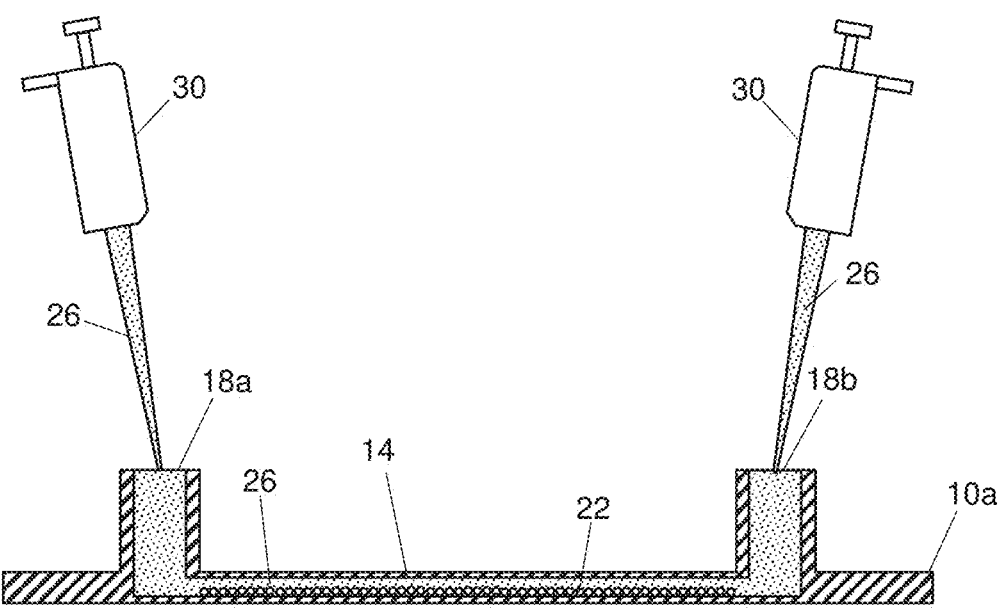
Figure 9B:
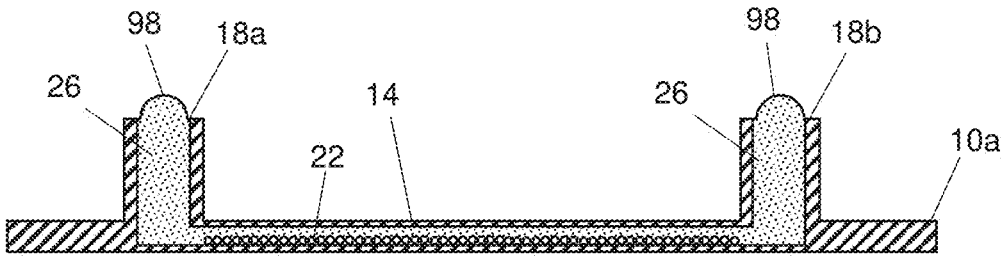
Figure 9E:
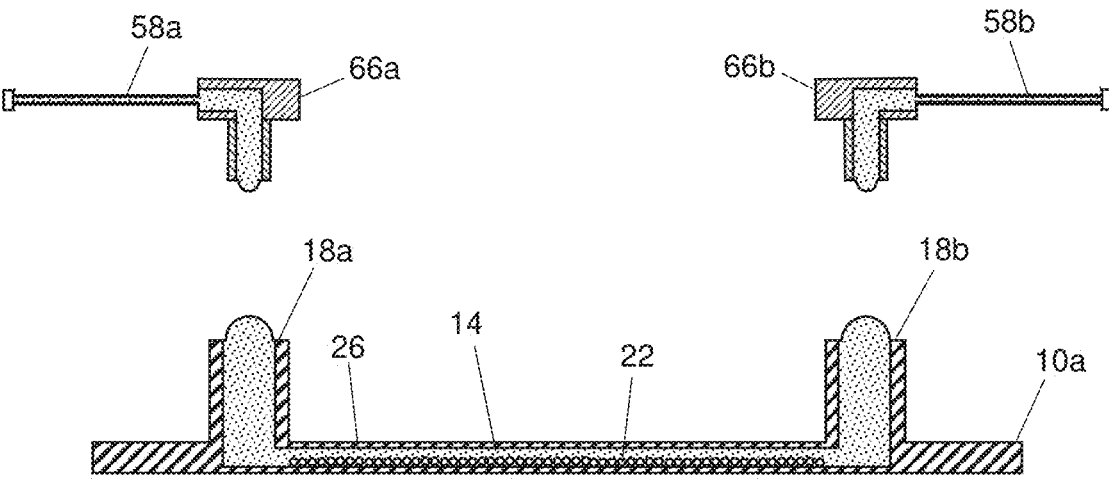
Figure 9F:
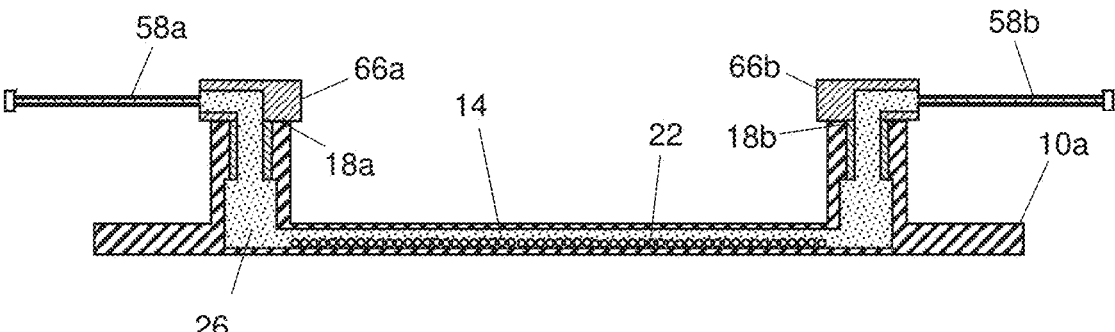
Figures 9G, 10:
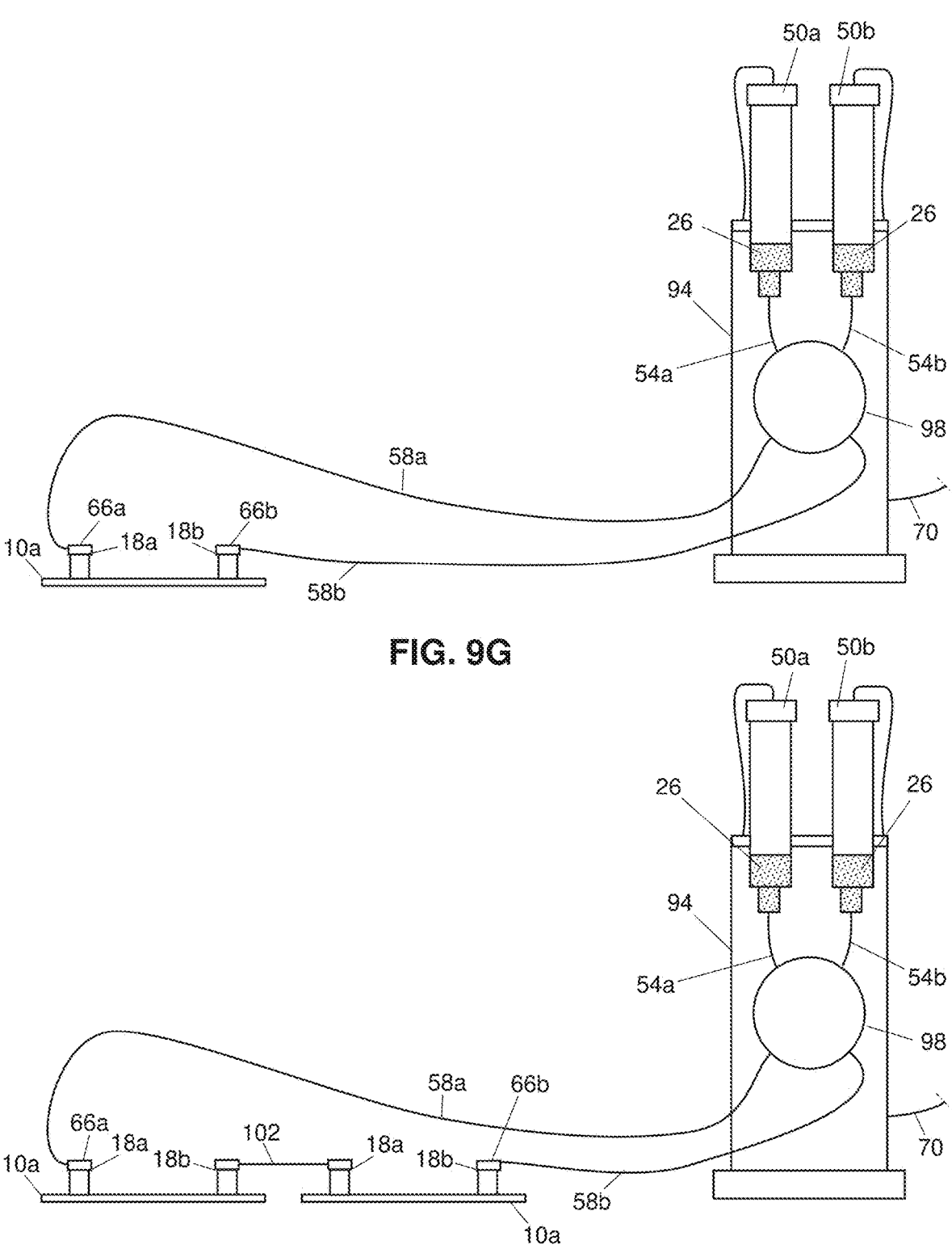

After the degassing, the pump can be placed in fluid communication with the port(s) of the microfluidic chip(s) such that the pump can pump liquid through the channel(s) thereof. To do so while mitigating the risk of introducing gas into the system, for each of the port(s) of the microfluidic chip to which one of the port connector(s) is to be connected, growth medium (e.g., any of those described above) can be added to the port such that the growth medium forms a convex meniscus (e.g., 98) protruding out of the port (FIGS. 9A and 9B). For example, greater than or equal to any one of, or between any two of, 20, 25, 30, 35, 40, 45, 50, 55, or 60 μL (e.g., at least 45 μL) of growth medium can be introduced into each of those port(s) to form such a convex meniscus. Additionally, growth medium (e.g., any of those described above) can be added to an outlet of each of the port connector(s) (e.g., with the outlet facing upward and the outlet tube to which the port connector is coupled clamped to mitigate the risk of leakage) such that the growth medium also forms a convex meniscus protruding out of the port connector (FIGS. 9C and 9D). For example, greater than or equal to any one of, or between any two of, 5, 10, 15, 20, 25, 30, 35, or 40 μL (e.g., at least 15 μL) of growth medium can be added to the outlet of each of the port connector(s) to form such a convex meniscus. Each of the port connector(s) can then be coupled to one of the port(s) such that liquid can be introduced into or received out of the port through the outlet tube coupled to the port connector (FIGS. 9E-9G). For example, as shown, for each of the channel(s) having first and second ports that are each disposed at a respective one of the ends of the channel, the first and second port connectors of one of the perfusion set(s) can be coupled to the first and second ports, respectively, at the ends of the channel such that liquid dispensed from the perfusion set can flow through one of its outlet tubes to one of the ports, through the channel, out of the other of the ports, and through the other of the outlet tubes.

In the embodiment shown, a single perfusion set is placed in fluid communication with a single channel. When there are multiple channels—whether of a single microfluidic chip or multiple microfluidic chips—the perfusion set(s) can be coupled to the microfluidic chip(s) in any suitable manner for series and/or parallel flow of the test liquid(s) through the channels.

Referring to FIG. 10, for series flow, in some embodiments at least two of the channels—whether of a single microfluidic chip or, as shown, of multiple microfluidic chips—can be connected in series such that liquid can flow successively through the connected channels. To illustrate, for two or more channels that each have first and second ports that are each disposed at a respective one of the ends of the channel, as shown the first port connector of one of the perfusion set(s) can be coupled to the first port of a first one of the channels, the second port connector of the perfusion set can be coupled to the second port of a last one of the channels, and one or more channel connectors (e.g. 102) can each couple the second port of one of the channels to the first port of another one of the channels. Liquid can thus enter the first channel through the first port connector, flow successively through the channels, and exit the last channel via the second port connector, and vice versa (e.g., to assess interactions as a therapeutic reagent flows through channels containing different types of target cells).

For parallel flow, there can be two or more flow paths that each include a single one of the channels or multiple channels connected in series (e.g., as described above). With a single perfusion set, the perfusion set can have multiples tubes and port connectors such that each of the port connectors is coupled to a port in fluid communication with the channel(s) of a respective one of the flow paths. Liquid dispensed from the perfusion set can thus be divided into a plurality of portions that each flow through a respective one of the flow paths without flowing through another one of the flow paths. With multiple perfusion sets—each of which can, but need not, contain a different test liquid—parallel flow can be achieved by coupling the port connector(s) of each of the perfusion sets to one of the port(s) that are in fluid communication with the channel(s) of a respective one of the flow paths. As such, for each of the perfusion sets, liquid dispensed from the perfusion set can flow through a respective one of the flow paths without flowing through another one of the flow paths. Parallel flow can be used to independently assess different target cell-therapeutic reagent interactions across the different flow paths.

Figure 11:
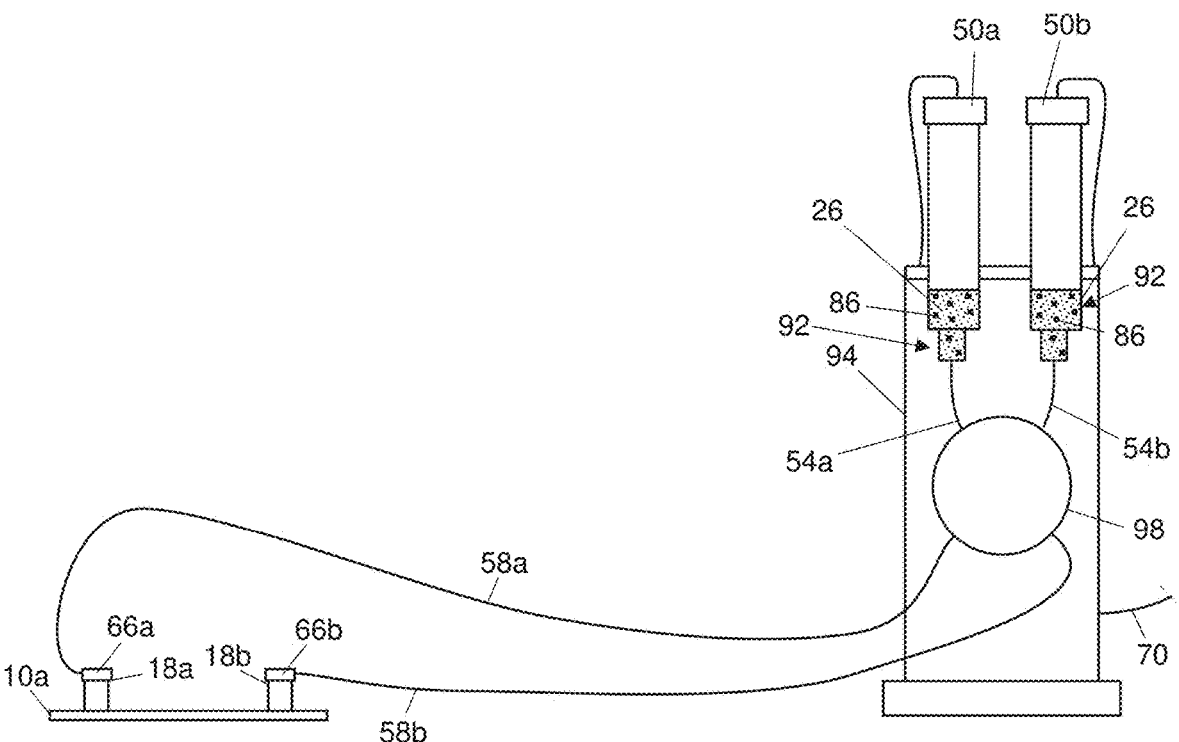
FIG. 11 illustrates the coupled fluidic unit and perfusion set of FIGS. 8A and 8B while in fluid communication with the microfluidic chip of FIG. 1A, where a test liquid containing a therapeutic reagent is placed in each of the reservoirs of the perfusion set.

Referring to FIG. 11, after placing the pump in fluid communication with the port(s) of the microfluidic chip(s), the test liquid(s) can be placed in fluid communication with the pump such that the pump is configured to flow each of the test liquid(s) through at least one of the channel(s) of the microfluidic chip(s). For example, as shown, each of the test liquid(s) that comprises a therapeutic reagent can be introduced into at least one of the reservoir(s) of a respective one of the perfusion set(s).

Figure 12:
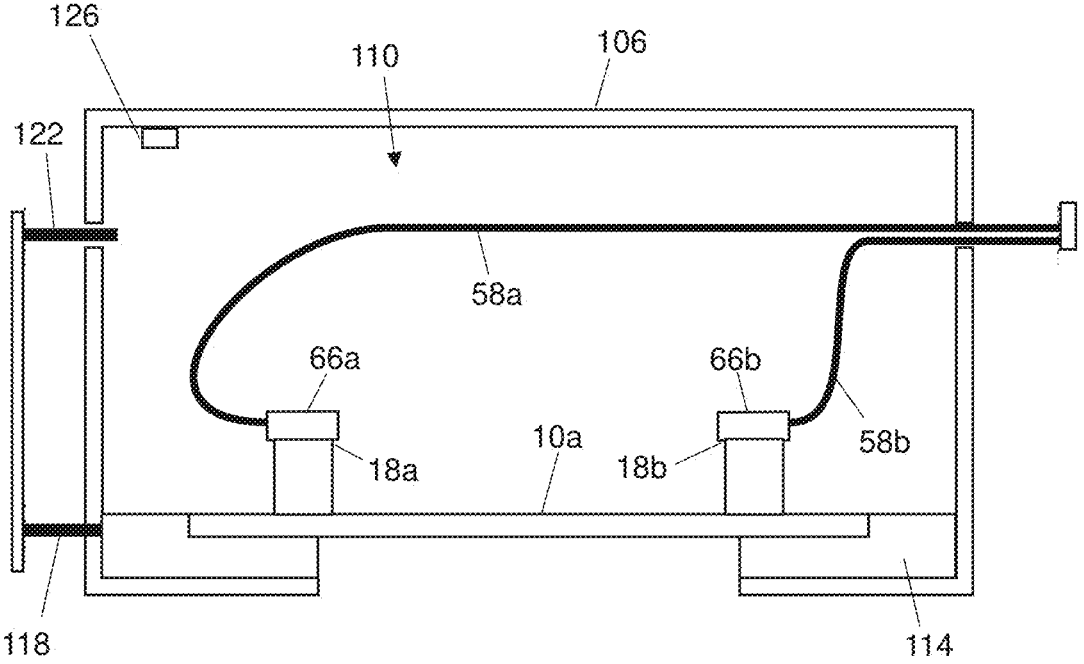
FIG. 12 illustrates the microfluidic chip of FIG. 1A disposed in a stage-top incubator while in fluid communication with the perfusion set of FIGS. 8A and 8B.
Figure 13:
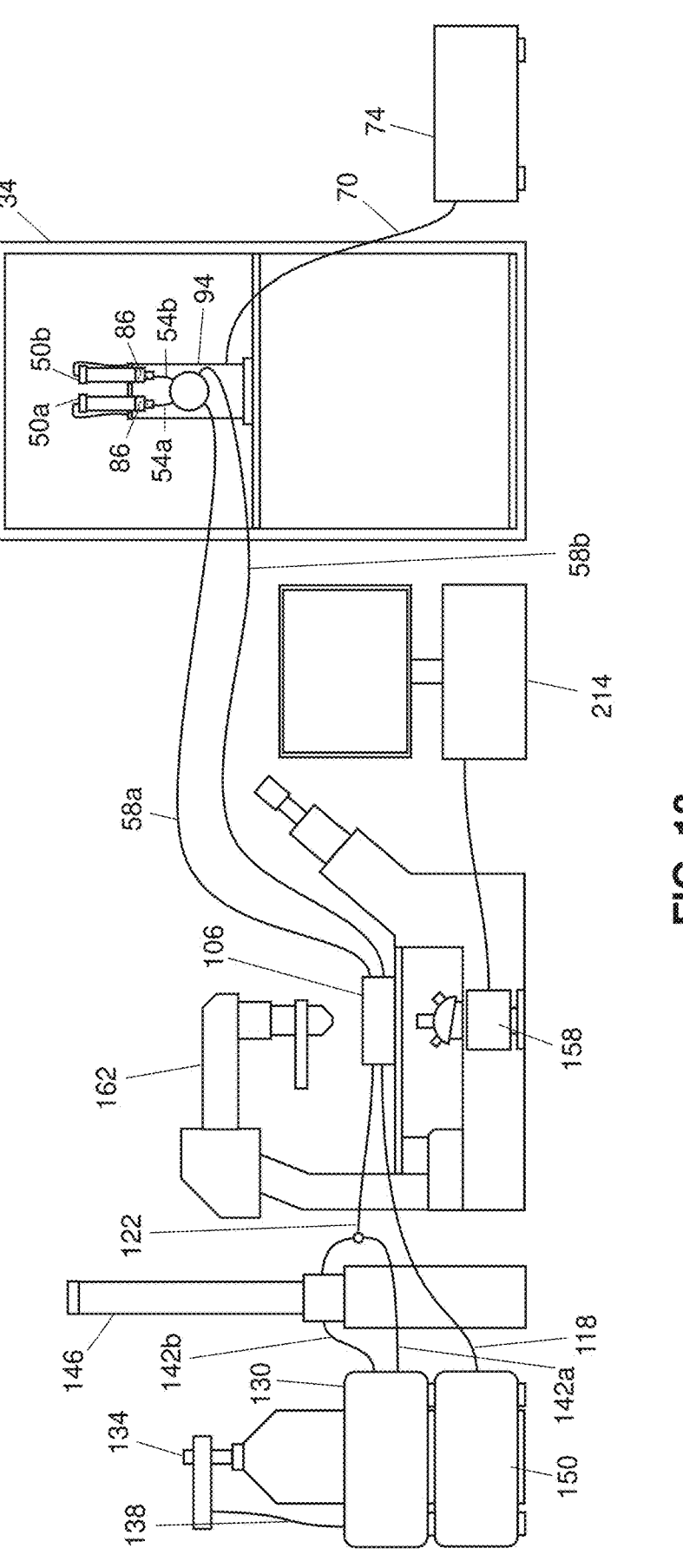
FIG. 13 illustrates the system of FIG. 5, where the coupled fluidic unit and perfusion set of FIGS. 8A and 8B are disposed in the incubator of FIG. 3C while coupled to the pump and while in fluid communication with the microfluidic chip of FIG. 1A that is disposed in the stage-top incubator such that the pump is configured to flow the therapeutic reagent in the reservoirs of the perfusion set over the cultured target cells in the channel of the microfluidic chip.

Turning to FIG. 12, some systems comprise a stage-top incubator 106 that comprises a chamber 110 configured to receive the microfluidic chip(s) and hold the chip(s) while the pump is in fluid communication with their port(s). Stage-top incubator 106 can be used to control the environment in which the test liquid(s) flow over the cultured target cells to, for example, mimic conditions that may exist in vivo. To do so, stage-top incubator 106 can be configured to heat the microfluidic chip(s) while the microfluidic chip(s) are disposed in chamber 110, such as with a heating plate 114 that is in thermal communication with the chamber. Referring additionally to FIG. 13, heating plate 114 can be in electrical communication with a temperature controller 150 (e.g., via a cable 118) of system 42 that can be configured to control a heat output of the heating plate based on, for example, the temperature in stage-top incubator 106's chamber 110 and the target chamber temperature. Furthermore, system 42 can comprise one or more gas sources 134 that can each be in fluid communication with chamber 110 of stage-top incubator 106 to control the gaseous composition in the chamber, such as a carbon dioxide ($CO_2$) source, an oxygen ($O_2$) source, a nitrogen ($N_2$) source, and/or an air source containing compressed air (e.g., in which a pressure of the air is greater than ambient pressure). Such fluid communication can be achieved via at least a gas mixer 130 of system 42 that can be in fluid communication with gas source(s) 134 (e.g., via gas source tube 138) and configured to, when there are multiple gas sources (e.g., of different gases), mix the gases in desired proportions (e.g., to mimic in vivo conditions associated with hypoxia, normoxia, or hyperoxia), where gas from the gas mixer can be directed through outlet tube 122 to stage-top incubator 106's chamber 110. System 42 can also comprise a humidifier 146 in fluid communication with stage-top incubator 106's chamber 110 to control the humidity in the chamber (e.g., to be anywhere between 0% and 100%). To illustrate, humidifier 146, which can contain water, can be in fluid communication with gas mixer 130 such that at least a portion of the gas from the gas mixer can flow through the humidifier—thereby increasing the humidity of that portion of gas—before entering stage-top incubator 106's chamber 110. As shown, a first gas connecting tube 142*a* can direct a first portion of the gas from gas mixer 130 to gas outlet tube 122 without flowing through humidifier 146 and a second gas connecting tube 142*b* can direct a second portion of the gas from the gas mixer through the humidifier, after which the second portion of gas can combine with the first portion of gas and flow to chamber 110 of stage-top incubator 106 through the gas outlet tube. Gas mixer 130 can control the relative proportions of gas exiting through first and second gas connecting tubes 142*a* and 142*b* to thus control the amount of gas flowing through humidifier 146 and thus the rate at which moisture is introduced into stage-top incubator 106's chamber 110. Stage-top incubator 106 can comprise one or more sensors 126 that are configured to measure, for example, a temperature and/or humidity in the stage-top incubator to control the heat output of heating plate 114 and the extent to which humidifier 146 adds moisture to the gas entering the chamber (e.g., by controlling the proportion of gas from gas mixer 130 that flows through the humidifier). And stage-top incubator 106 can be smaller than incubator 34 (e.g., with incubator 34's chamber 38 being larger than the stage-top incubator's chamber), as it need not hold larger equipment like fluidic unit 94 and its smaller form factor allows it to be readily placed on measuring instruments such as the below-described microscope 162. Incubator 34's chamber 38 can also be in fluid communication with one or more gas sources (e.g., a $CO_2$ source, $N_2$ source, $O_2$ source, and/or compressed air source) and/or a humidifier that can, but need not, be the same as those in fluid communication with stage-top incubator 106's chamber 110, where such fluid communication can, but need not, be achieved in the same way the stage-top incubator's chamber is in fluid communication with its gas source(s) and/or humidifier (e.g., with a mixer). This can allow reservoir(s) 50a and 50b of perfusion set 46 disposed in chamber 38 of incubator 34 to exposed to the same physiologically-relevant gaseous composition as the composition that the microfluidic chip(s) are exposed to in stage-top incubator 106's chamber 110.

With the equipment used for flowing the test liquid(s) through the channel(s) of the microfluidic chip(s) connected to the microfluidic chip(s) and the microfluidic chip(s) optionally disposed in the chamber (e.g., 110) of the stage-top incubator (e.g., 106), the flow experiment of the assay can be performed. Accordingly, and referring to FIGS. 14A-14D, some methods comprise, for each of the test liquid(s) that each comprise a therapeutic reagent, flowing the test liquid over the cultured target cells in at least one of the channel(s), which can be achieved using the pump in the manner described above. Because an administered therapeutic reagent may flow over target cells in vivo, flowing each test liquid and thus the therapeutic reagent contained therein over cultured target cells can better mimic the physiological conditions under which the therapeutic reagent will encounter target cells in the body, compared to conventional assays that assess the interactions between therapeutic reagents and targets cells under static conditions. For example, a therapeutic reagent's flow over target cells can impact its ability to bind with and/or infiltrate the target cells, which is an impact that static assays cannot ascertain. Accordingly, the assays in which each therapeutic reagent flows over target cells may more accurately reflect the interactions that the therapeutic reagent will have with the target cells when administered in vivo.

Figure 14A:
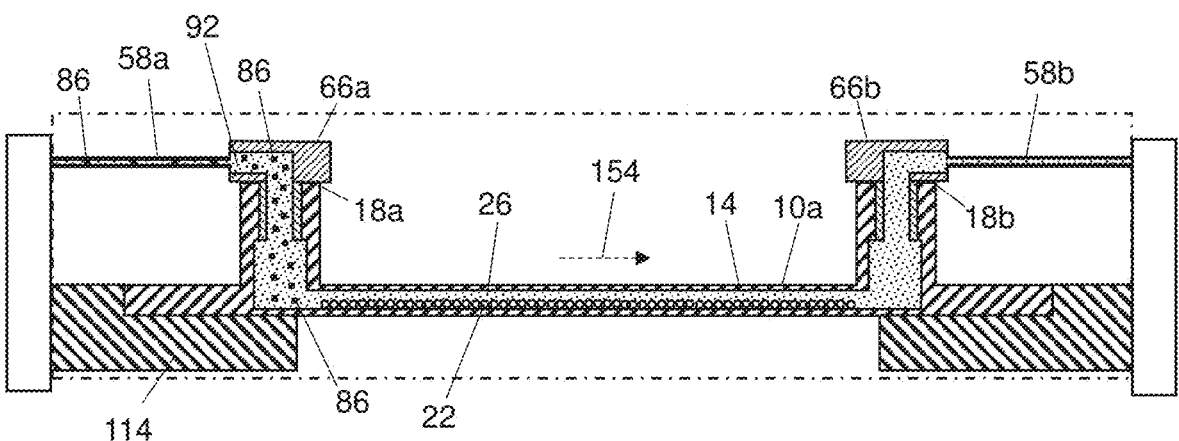
FIGS. 14A-14D illustrate the flow of the therapeutic reagent held by the perfusion set of FIGS. 8A and 8B over the target cells in the channel of the microfluidic chip of FIG. 1A while the microfluidic chip is disposed in the stage-top incubator of FIG. 12.
Figure 14B:
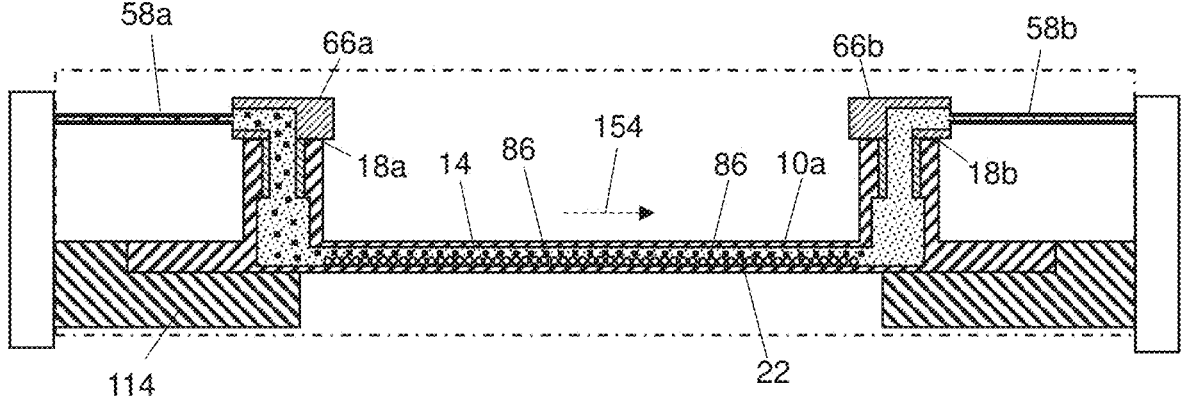
Figure 14C:
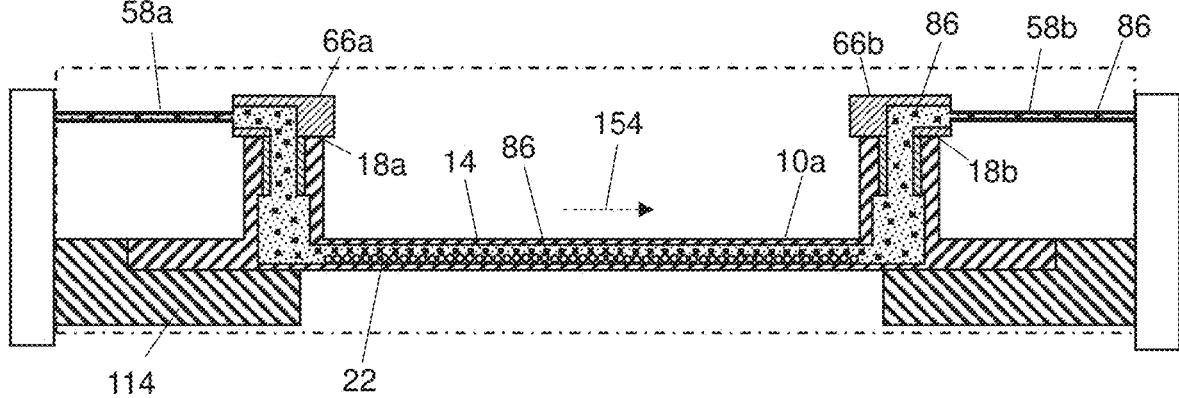

The manner in which each test liquid flows over cultured target cells in at least one of the channel(s) can be controlled to mimic the physiologically-relevant conditions for the particular target cells and therapeutic reagent contained in the test liquid. To illustrate, FIGS. 14A-14C depict flow in which the test liquid enters the channel through a first end of one of the channel(s) (e.g., after flowing through the first outlet tube, first port connector, and first port as described above) (FIG. 14A), flows through the channel in a direction (e.g., 154) toward a second end of the channel (FIG. 14B), and exits the channel through the channel's second end (e.g., to exit the microfluidic chip through the second port and second port connector and flow through the second outlet tube as described above) (FIG. 14C). In the embodiment shown, this flow can be unidirectional (e.g., with the test liquid in the channel continuously flowing toward the channel's second end). However, as described above, in other embodiments the flow can be pulsatile (e.g., with flow of the test liquid in the channel occurring at intervals) to, for example, mimic flow in the arterial, venous, and/or lymphatic systems, or oscillatory (e.g., with the test liquid in the channel periodically changing directions to flow towards the channel's second end in one state and toward the channel's first end in another state) to, for example, mimic the flow of cerebrospinal fluid in the spinal canal. Furthermore, the flow can be controlled such that a shear stress between the test liquid and a surface in the channel can be less than or equal to any one of, or between any two of, 100, 90, 80, 70, 60, 50, 40, 30, 20, 10, or 1 dyne per square centimeter ($dyn/cm^2$) (e.g., between 1 and 100 $dyn/cm^2$), as appropriate for the modeled physiological environment. To illustrate, the shear stress can be between 1 and 22 $dyn/cm^2$ to mimic the conditions in an aorta, between 10 and 70 $dyn/cm^2$ to mimic the conditions in an artery, between 1 and 6 $dyn/cm^2$ to mimic the conditions in a vein, or between 3 and 95 $dyn/cm^2$ to mimic the conditions in a capillary. Other shear stresses may be appropriate for different mimicked physiological environments.

When there are multiple channels, as noted above at least a portion of at least one (up to and including each) of the test liquid(s) can flow successively through at least two of the channels (e.g., that are connected in series). Such series-connected channels can each contain a respective type of the cultured target cells to, for example, better mimic the conditions that the test liquid's therapeutic reagent may encounter in vivo, which may include flow over multiple types of cells. And as also described above, there can be parallel flow through different flow paths that each include one or more of the channels to assess different target cell-therapeutic reagent interactions, where two or more portions of a single test liquid or multiple test liquids each flow through the channel(s) of a respective one of the flow paths and not through the channel(s) of another one of the flow paths. For example, the one or more test liquids can comprise two or more test liquids, where for each of the test liquids the therapeutic reagent of the test liquid can be different than the therapeutic reagent of each other of the test liquids and the channel(s) through which the test liquid flows can be different than the channel(s) through which each other of the test liquids flows. This can allow for an assessment of how the different therapeutic reagents interact with the cultured target cells. Additionally, when there are multiple types of cultured target cells in different channels—whether series-connected or parallel—and the same therapeutic reagent flows over the different types of target cells, the assay can be used to assess how different cell types interact with a given therapeutic reagent to, for example, investigate label expansion of the therapeutic reagent (e.g., to assess if there are any beneficial effects with respect to other cells than those the therapeutic reagent was initially designed for).

Furthermore, to promote fidelity to the expected physiological environment, each of the test liquid(s) can be heated and/or the cultured target cells over which the test liquid flows can be heated while the test liquid flows over the cultured target cells. To do so, the fluidic unit containing the test liquid can be disposed in the chamber of the incubator and/or the microfluidic chip(s) comprising the channel(s) in which the test liquid flows can be disposed in the chamber of the stage-top incubator and a temperature in the incubator's chamber and/or a temperature in the stage-top incubator's chamber can be greater than or equal to any one of, or between any two of, 30, 31, 32, 33, 34, 35, 36, 37, 38, 39, or 40° C. (e.g., at least 35° C., such as about 37° C., which is the typical temperature of a human body). And when microfluidic chip(s) are disposed in the stage-top incubator's chamber, some methods comprise directing one or more gases from one or more gas sources (e.g., 134)—such as $CO_2$ from a $CO_2$ source, $O_2$ from an $O_2$ source, $N_2$ from an $N_2$ source, and/or air from an air source in which a pressure of the air is higher than ambient pressure—and/or moisture into the stage-top incubator's chamber as described above to achieve a desired environment. Likewise, some methods comprise directing one or more gases from one or more gas sources—such as $CO_2$ from a $CO_2$ source, $O_2$ from an $O_2$ source, $N_2$ from an $N_2$ source, and/or air from an air source in which a pressure of the air is higher than ambient pressure—and/or moisture into the chamber of the incubator containing the reservoir(s) of the perfusion set such that the reservoir(s) are exposed to a desired environment as well.

Figure 14D:
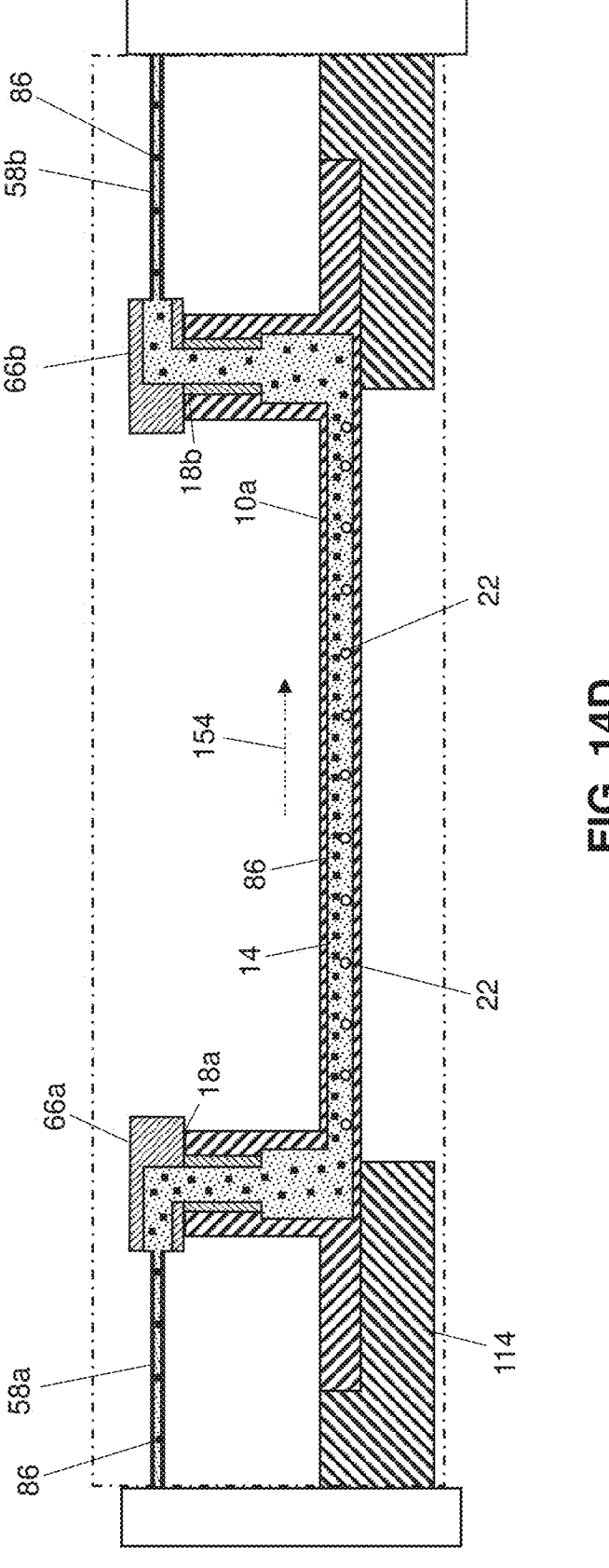

The therapeutic reagent of each of the test liquid(s) may interact with the cultured target cells over which the therapeutic reagent flows. This dynamic assay can be used to assess interactions between a wide variety of therapeutic reagents and target cells to, for example, evaluate the effectiveness of such therapeutic reagents. To illustrate, the assay can be used to evaluate the potency, identity, avidity, specificity, and/or mechanism of action of the therapeutic reagent of each of the test liquid(s), such as to determine an extent to which the therapeutic reagent of the test liquid kills, heals, binds to, and/or infiltrates the cultured target cells. Changes in protein expression, transcription, translation, post-translational modifications, cellular proliferation, cellular differentiation, and/or cellular fusion in or of the cultured target cells can be assessed after exposure to the therapeutic reagent, as can the intake and processing of vectors, the translocation and deletion of nucleic acids, the release of cytokines, chemokines, and/or growth factors, and/or the like. In the embodiment shown and as explained above, for each of the test liquid(s), the cultured target cells in at least one of the channel(s) in which the test liquid flows can comprise cancer cells and the therapeutic reagent of the test liquid can comprise an anticancer agent such as lymphocytes (e.g., T-cells, NK cells, and/or B cells that can be engineered to kill the cancer cells); as shown in FIG. 14D, the anticancer agent (e.g., lymphocytes) can kill at least a portion of the cancer cells and/or attach to at least some of the cancer cells such that they accumulate in the channel in which the cancer cells were cultured. However, as noted above, in other embodiments the cultured target cells need not include cancer cells (e.g., to investigate treatments of other conditions). And the therapeutic reagent—whether an anticancer agent or a treatment for another condition—can comprise a composition other than lymphocytes, such as a small-molecule drug, an antimicrobial agent (e.g., antibacterial, antifungal, antiviral, and/or antiparasitic), exosomes, extracellular vesicles, nucleic acids such as DNA or RNA (e.g., miRNA, siRNA, shRNA, and/or the like) that each can but need not be part of a virus, blood (e.g., peripheral blood, cord blood, pooled blood, and/or the like, whether or not modified), engineered cells, plasmids, vectors, cell and/or tissue lysates, proteins, peptides, aptamers, monoclonal antibodies, lipid nanoparticles, liposomes, a vaccine, and/or the like. For example, for gene therapy in which the therapeutic reagent comprises nucleic acids, the effectiveness of the therapy can depend at least in part in the nucleic acids' ability to infiltrate and accordingly manipulate the gene expression and/or biological properties of the target cells, whether through a carrier virus's infection of the target cells or, if the nucleic acids are not carried by viruses, flow-based transduction and/or transfection. With the nucleic acids flowing over the cultured target cells under physiologically-relevant conditions, the assay can be used to accurately assess the extent to which such infiltration and cell manipulation will occur in vivo.

As another example, the cultured target cells can be infected with a pathogen (e.g., a bacteria, virus, fungus, and/or the like) by, for example, flowing a liquid that includes the pathogen over the cultured target cells, which can additionally provide insight into how the pathogen infects the cultured target cells. In such embodiments, the test liquid(s) can each comprise an antimicrobial agent to screen for the antimicrobial's ability to stop the infection.

To further illustrate, the assay can be used to assess autologous and allogeneic therapies in which the therapeutic reagent comprises cells, such as blood cells, from an individual that can be modified to treat a condition and subsequently introduced back into the individual (e.g., for autologous therapy) or into other individuals (e.g., for allogeneic therapy). The interactions that occur during the assay can indicate whether the therapeutic reagent cells are potent and thus whether to culture more of the cells for use by the individual (e.g., for autologous therapy), to culture more of the cells for use by other individuals that can, but need not, be targeted based at least in part on the donor's genetics (e.g., for allogeneic therapy), to enroll the donor in a clinical trial (e.g., for cohort screening), to identify epigenetic differences, and/or the like.

The therapeutic reagent can also comprise a combination of agents to assess, for example, the combined effectiveness of the agents (e.g., if one was insufficient on its one). As an illustration, the therapeutic reagent can comprise nucleic acids (e.g., for gene therapy) and a chemotherapy drug to assess the combination's effectiveness against cultured target cells that include recalcitrant cancer cells.

In some embodiments in which there are multiples types of target cells as described above, the assay can also be used to accurately assess how the therapeutic reagent of each test liquid that flows over multiple types of target cells affects both a primary type of target cells (e.g., the type of target cells that the therapeutic reagent is designed to interact with) and one or more secondary types of target cells (e.g., the type(s) of target cells that the therapeutic reagent is not designed to interact with). For example, the secondary type(s) of target cells can be healthy cells and how the therapeutic reagent interacts with those target cells can be assessed such that the assay can be used to determine the safety of the therapeutic reagent (e.g., if there are any adverse side effects with the secondary type(s) of target cells) in addition to its efficacy when interacting with the primary type of target cells.

For each of the test liquid(s), flowing the test liquid over the cultured target cells can be performed for any suitable amount of time to allow interactions between the test liquid's therapeutic reagent and cultured target cells to manifest, such as for greater than or equal to any one of, or between any two of, 1, 2, 4, 6, 8, 10, 12, 14, 16, 18, 20, 22, 24, 26, 28, or 30 days (e.g., between 14 and 28 days).

To assess the target cell-therapeutic reagent interactions, some methods comprise, for each of the test liquid(s), while flowing the test liquid over the cultured target cells, capturing data indicative of an interaction between the target cells over which the test liquid flows and the therapeutic reagent of the test liquid. Any suitable data-capturing technique can be used, such as via imaging, electrical measurements (e.g., of impedance, resistance, capacitance, voltage, and/or the like) that are indicative of the target cell-therapeutic reagent interactions, an enzyme-linked immunosorbent assay (ELISA), surface plasmon resonance, sequencing, Raman spectroscopy, luminescence, flow cytometry, and/or the like. Some of such data-capturing techniques that require a sample for analysis can be performed during the flowing by, for each of the test liquid(s), taking a sample of liquid that flowed through one or more of the channel(s) (e.g., from one of the reservoir(s) of the perfusion set, if used, after the sample flowed to the reservoir after passing through those channel(s)). In the embodiment shown, imaging can be used, which need not involve such sampling.

To image the interactions, as shown in FIG. 13 system 42 can comprise one or more cameras 158 and a microscope 162, where the microfluidic chip(s) can be positioned relative to the camera(s) (e.g., while disposed in chamber 110 of stage-top incubator 106 that can be placed on the microscope) such that each of the camera(s) can capture a sequence of images (e.g., a video) of at least a portion (up to and including substantially all) of at least one of the channel(s) of at least one of the microfluidic chip(s) through the microscope. Microscope 162 can thus enlarge the images of the channel(s) that camera(s) 158 can capture to facilitate observation of the target cell-therapeutic reagent interactions. With the microfluidic chip(s) so-positioned, for each of the test liquid(s), capturing data indicative of an interaction between the target cells over which the test liquid flows and the therapeutic reagent of the test liquid can comprise capturing one or more sequences of images (e.g., one or more videos), where each of the sequence(s) can be captured with a respective one of the camera(s) (e.g., 158) and can be of an area containing at least a portion (up to and including substantially all) of at least one of the channel(s) in which there are cultured target cells over which the test liquid flows. For each sequence, any suitable interval between images of the sequence can be used to detect the interactions under investigation. For example, each of camera(s) 158 can be configured to capture a sequence of images at a frame rate that is greater than or equal to any one of, or between any two of, 100, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, or 25,000 frames per second (fps). The extent to which the available frame rate of the camera(s) is used can depend on the capture rate required to adequately observe the target cell-therapeutic reagent interactions. To illustrate, higher frame rates (e.g., such that the sequence of images appear as a temporally-continuous video) can be well-suited to capture, for example, the initial binding of the therapeutic reagent to the cultured target cells, such as a frame rate where each camera captures greater than or equal to any one of, or between any two of, 50, 60, 70, 80, 90, 100, 500, 1,000, or 2,000 of the images of the sequence per second (e.g., at least 70 images, such as any of the above-described frame rates, per second). Lower frame rates—which can reduce data demands—may be appropriate to capture other interactions like the killing of cultured target cells, such as a frame rate where each camera captures less than or equal to any one of, or between any two of, 20, 18, 16, 14, 12, 10, 8, 6, 4, or 2 images of the sequence per minute (e.g., less than or equal to 4 images per minute). And different frame rates can be used at different points during the assay, such as one of the above-described higher frame rates over a first period during which each test liquid flows over the cultured target cells and one of the above-described lower frame rates over a second period (e.g., that is subsequent to the first period) during which each test liquid flows over the cultured target cells.

Figure 15A:
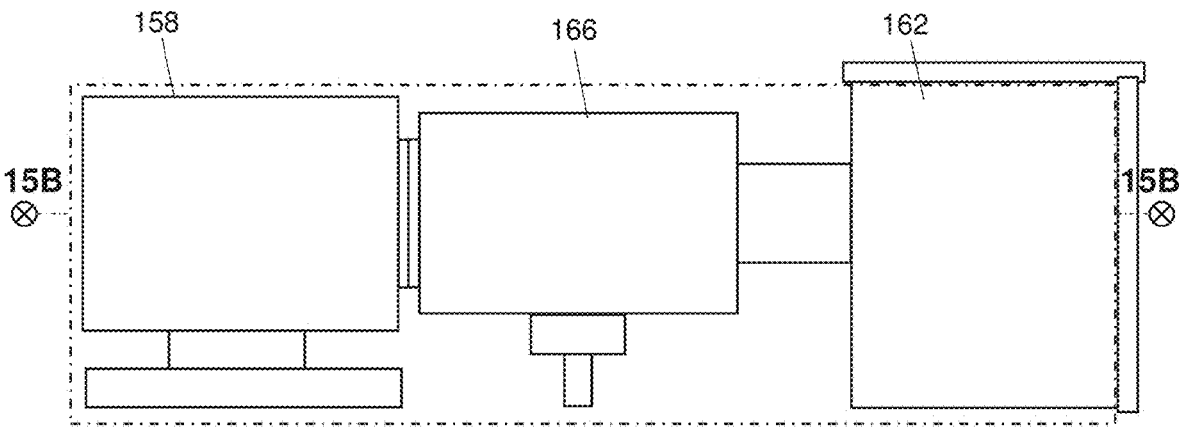
FIG. 15A is a side view of the camera of the system of FIG. 5 positioned relative to the microscope of the system, where an image splitter is disposed between the camera and the microscope.
Figure 15B:
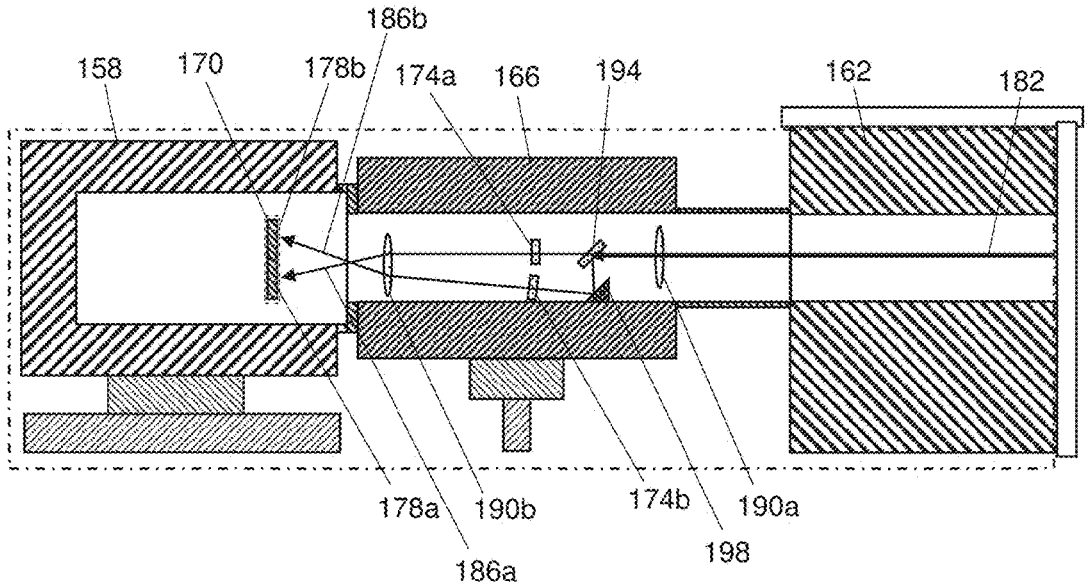
FIG. 15B is a sectional view of the camera, image splitter, and microscope of the system of FIG. 5 taken along line 15B-15B of FIG. 15A and illustrates how the image splitter splits light emitted by the cultured target cells and therapeutic reagent in the channel of the microfluidic chip of FIG. 1A and how the different light portions are received by different portions of the camera's image sensor.

As explained above, fluorescence imaging can be employed, where from staining the cultured target cells can include a first fluorescent agent having an emission spectrum that comprises a first peak wavelength and, for each of the test liquid(s), the therapeutic reagent of the test liquid can include a second fluorescent agent having an emission spectrum that comprises a second peak wavelength that is at least 10% different than the first peak wavelength. Thus, and referring additionally to FIGS. 15A and 15B, for each of the sequence(s) of images, capturing the sequence of images can comprise receiving light (e.g., 182) emitted by the first and/or second fluorescent agents (e.g., after passing through the microscope) at an image sensor (e.g., 170) of the camera that captures the sequence of images. Because the emission spectra from the therapeutic reagent and cultured target cells can be different, the therapeutic reagent and cultured target cells can be distinguished to assess the interactions therefrom.

Figures 16A, 16B:
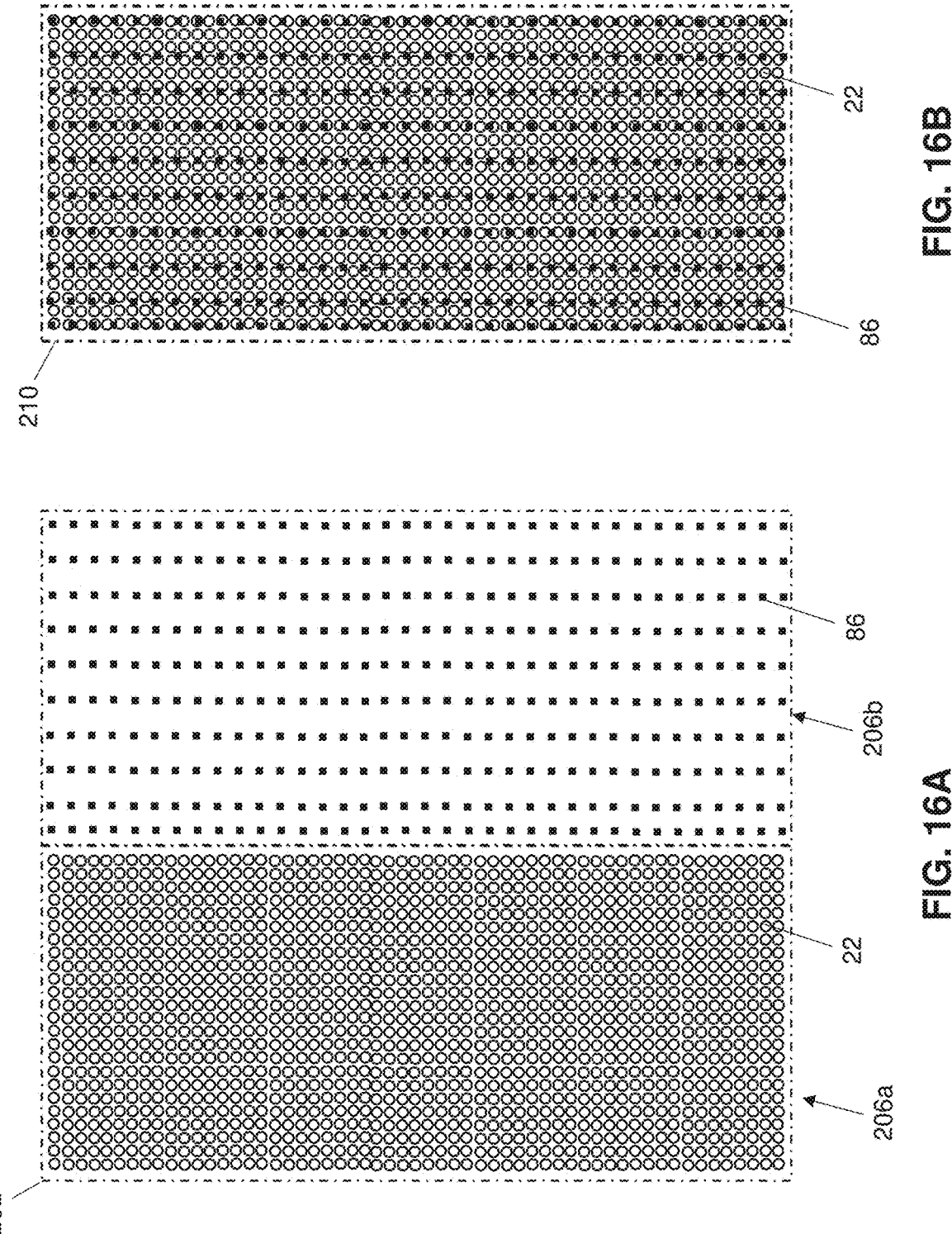
FIGS. 16A and 16B illustrate how different portions of an image captured by different portions of the image sensor of the camera of the system of FIG. 5 are superimposed to depict the therapeutic reagent over the cultured test cells in the channel of the microfluidic chip of FIG. 1A.
Figure 16C:
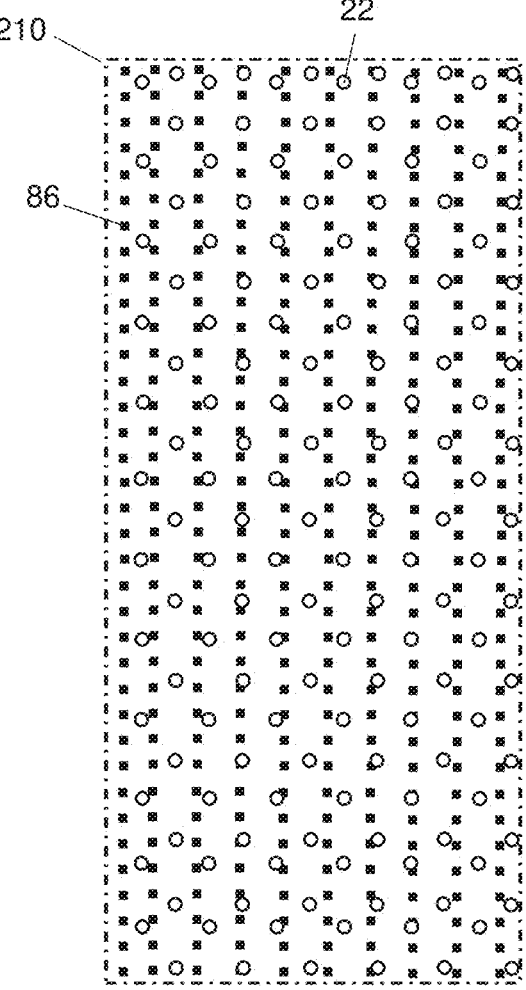
FIG. 16C illustrates a superimposed image generated in accordance with the procedure in FIGS. 16A and 16B after the therapeutic reagent has killed target cells in the channel of the microfluidic chip of FIG. 1A.

Preferably, each of camera(s) 158 is a monochromatic camera, which can better capture high-resolution images at a frame rate for observation of target cell-therapeutic reagent interactions than a color camera. When the cultured target cells and therapeutic reagent of each test liquid are distinguished based on color (e.g., based on their different emission spectra), system 42 can also comprise first and second optical filters 174a and 174b that can be part of a beam splitter 166 to allow one or more monochromatic cameras 158 to make those color-based distinctions. First optical filter 174a can be transmissive over a first spectrum and second optical filter 174b can be transmissive over a second spectrum that is different than the first spectrum. For example, the first spectrum over which first optical filter 174a is transmissive can include the first peak wavelength of the first fluorescent agent's emission spectrum (but not the second peak wavelength of the second fluorescent agent's emission spectrum) and the second spectrum over which second optical filter 174b is transmissive can include the second peak wavelength of the second fluorescent agent's emission spectrum (but not the first peak wavelength of the first fluorescent agent's emission spectrum) (e.g., with the first spectrum including a wavelength of 525 nm but not 625 nm and the second spectrum including a wavelength of 625 nm but not 525 nm, or vice versa). Beam splitter 166 can further comprise one or more optical components such as one or more (e.g., two or more) lenses 190a and 190b, a dichroic mirror 194, and a mirror 198 arranged such that, for at least one (up to and including each) of the channel(s), either: (1) for at least one of camera(s) 158, a first portion of light (e.g., 186a) emitted from the channel that passes through the first filter strikes a first part 178a of the camera's image sensor 170 and a second portion of light (e.g., 186b) emitted from the channel that passes through the second filter strikes a second part 178b of the camera's image sensor (e.g., as shown), or (2) for some embodiments where the one or more cameras comprise a plurality of cameras, the first portion of light strikes the image sensor of a first one of the cameras, and the second portion of light strikes the image sensor of a second one of the cameras. Because first and second optical filters 174a and 174b can be transmissive over spectra that include wavelengths associated with the first and second fluorescent agents, respectively, the first and second portions of light—which can be emitted by the fluorescent agents—can be light from the cultured target cells that include the first fluorescent agent and the therapeutic reagent that includes the second fluorescent agent, respectively. That is, for embodiments in which the image sensor of each of the camera(s) receives light emitted by both the first and second fluorescent agents, for each of the sequence(s) of images, receiving the light at the image sensor of the camera that captures the sequence of images can comprise directing the first portion of the light that includes the first peak wavelength but not the second peak wavelength to the first part (e.g., 178a) of the camera's sensor and the second portion of the light that includes the second peak wavelength but not the first peak wavelength to the second part (e.g., 178b) of the camera's sensor (e.g., as shown). Accordingly, as shown in FIG. 16A, for each of the images of each of the sequence(s) of images, a first portion (e.g., 206a) of the image (e.g., 202) captured by the first part of the image sensor can include cultured target cells (but not the therapeutic reagent) and a second portion (e.g., 206b) of the image captured by the second part of the image sensor can include the therapeutic reagent (but not the cultured target cells). Or, for some embodiments where, for each of the test liquid(s), the one or more sequences of images comprise a plurality of sequences of images and the one or more cameras comprise a plurality of cameras, for a first one of the sequences captured with a first one of the cameras, receiving light from the first and/or second fluorescent agents at the image sensor of the first camera can comprise receiving the first portion of light but not the second portion of light at the first camera's image sensor and, for a second one of the sequences captured with a second one of the cameras, receiving light from the first and/or second fluorescent agents at the image sensor of the second camera can comprise receiving the second portion of light but not the first portion of light at the second camera's image sensor. In such embodiments, the first sequence of images captured with the image sensor of the first camera can include cultured target cells (but not the therapeutic reagent flowing over the cultured target cells in the first sequence) and the second sequence of images captured by the image sensor of the second camera can include the therapeutic reagent that flows over the cultured target cells in the first sequence (but not those cultured target cells). For embodiments in which an image sensor of each of the camera(s) receives both the first and second portions of light, some methods comprise processing each of the captured sequence(s) of images at least by superimposing the first and second portions of each of the images such that, as shown in FIGS. 16B and 16C, the processed image (e.g., 210) shows cultured target cells and the therapeutic reagent to ascertain the interactions therebetween (FIG. 16C). And for some embodiments in which, for each of the test liquid(s), there are multiple sequences of images and cameras with the first sequence including the cultured target cells and the second sequence including the therapeutic reagent that flows over the cultured target cells of the first sequence, the first and second sequences of images can be superimposed to generate a sequence of images that includes both the cultured target cells and the therapeutic reagent.

In some methods, the data can be analyzed to determine, for example, the efficacy and/or safety of the therapeutic reagent of each of the test liquid(s). To illustrate, as noted above, some methods comprise, for each of the test liquid(s) and based at least in part on the captured data, determining an extent to which the therapeutic reagent of the test liquid kills the target cells over which the test liquid flows and/or an extent to which the therapeutic reagent of the test liquid binds to the target cells over which the liquid flows. The determination can be qualitative or quantitative. For example, each of the sequence(s) of images can be observed to qualitatively assess whether the amount of cultured target cells and/or therapeutic reagent in the images changed over time. Additionally or alternatively, the change in the amount of cultured target cells and/or in the amount of therapeutic reagent in the images can be quantitatively assessed by, for example, calculating the proportion of each of the images that includes light associated with cultured target cells (e.g., the first portion of light) and/or the proportion of each of the images that includes light associated therapeutic reagent (e.g., the second portion of light) and how the proportions change over time. A decreasing proportion of the images including light associated with the cultured target cells can indicate killing of the target cells and an increasing proportion of the images including light associated with the therapeutic reagent can indicate binding of the therapeutic reagent.

Furthermore, some methods can comprise capturing data indicative of an interaction between the target cells over which each test liquid flows and the therapeutic reagent of the test liquid after the flow experiment to further confirm, for example, the efficacy and/or safety of the therapeutic reagent. For example, when the above-described fluidic unit is employed, after the flowing at least one of the reservoir(s) can contain cultured target cells that detached from the channel(s) in fluid communication with the reservoir(s) (e.g., due to killing of the target cells) and/or at least a portion of the therapeutic reagent that had flowed through the channel(s) in fluid communication with the reservoir(s) but did not remain in the channel(s) (e.g., due to a failure to bind to the cultured target cells in the channel(s) under flow conditions). Accordingly, the concentration of target cells, the concentration of the therapeutic reagent, and/or the concentration of one or more compositions that may reflect target cell-therapeutic reagent interactions in at least one of the reservoir(s) after the flowing can be assessed, such as via an ELISA, flow cytometry, sequencing, spectroscopy, multi-photon microscopy, and/or the like. To illustrate, the concentration of the target cells and/or the concentration of the therapeutic reagent in at least one of the reservoir(s) after the flowing can be compared to the concentration of the target cells and/or the concentration of the therapeutic reagent in at least one of the reservoir(s) before the flowing to determine the performance of the therapeutic reagent.

In some methods, for each of the test liquid(s), at least a portion of the therapeutic reagent can be collected (e.g., from at least one of the reservoir(s) of the perfusion set, if employed) after the flowing and used in another flow-based assessment (e.g., a second flow-based assessment performed in the manner described above, with a test liquid comprising the collected therapeutic reagent flowing over cultured target cells that can be of the same type that the collected therapeutic reagent flowed over in the first flow-based assessment). An interaction between the collected therapeutic reagent and the cultured target cells in the second flow-based assessment can be assessed to, for example, evaluate the therapeutic reagent's therapeutic persistence (e.g., its ability to have an effect on multiple cells). For example, when the therapeutic reagent comprises lymphocytes such as T-cells, NK cells, and/or B cells and the cultured target cells—for both the first and second flow-based assessments—comprise cancer cells, the second flow-based assessment can reflect the lymphocytes' ability to continue to kill additional cancer cells (e.g., as reflected by the results of the second flow-based assessment) after previously killing cancer cells (e.g., in the first flow-based assessment). Determining therapeutic persistence can facilitate the formulation of an appropriate dose.

The determination of the efficacy and/or safety of the therapeutic reagent of each of the test liquid(s) can indicate whether the therapeutic reagent should be administered to individuals generally (e.g., in a further clinical trial), and can also be used for quality control during manufacturing of a therapeutic reagent (e.g., by conducting the assay with a sample of the manufactured therapeutic agent periodically during the manufacturing process). However, as noted earlier, the assay can also be used in personalized medicine in which the target cells that are cultured are from a patient. For such applications, some methods comprise determining, for each of the test liquid(s) and based at least in part on the captured data, whether to administer the therapeutic reagent of the test liquid to the patient (e.g., to select which of a plurality of therapeutic reagents tested in the assay). At least one of the therapeutic reagent(s) can then be administered to the patient.

In some methods, artificial intelligence, machine learning, and/or predictive analytics can be employed to analyze the captured data (e.g., that captured during and/or after the flowing) to determine, for example, the efficacy and/or safety of the therapeutic reagent of each of the test liquid(s). Such analytical tools can reduce the time needed to determine the relevant outcome(s) of the assay. Additionally, the captured data can be introduced into a data set that contains other data and is used by artificial intelligence, machine learning, and/or predictive analytics such that the data set includes additional information regarding physiologically-relevant conditions for use in other analyses.

EXAMPLES

The present invention will be described in greater detail by way of specific examples. The following examples are offered for illustrative purposes only and are not intended to limit the invention in any manner. Those of skill in the art will readily recognize a variety of noncritical parameters that can be changed or modified to yield essentially the same results.

Example 1

A dynamic potency assay was performed in which a test liquid containing T-cells that were stained with a Qtracker™ 625 (e.g., red) staining solution flowed over A549 lung carcinoma epithelial cells that were stained with a Qtracker™ 525 (e.g., green) staining solution and were cultured in a 0.4 mm-high channel of an Ibidi® Luer μ-Slide.

The test liquid was pumped through the channel using the Ibidi® Pump System that included a pump in fluid communication with a fluidic unit that had reservoirs that held the test liquid and were in fluid communication with the channel such that, as described above, the pump could drive the test liquid from the reservoirs through the channel. The Ibidi® Luer μ-Slide was disposed in the chamber of a stage-top incubator from Ibidi® while the test liquid flowed over the A549 cells, where a temperature in the chamber was maintained at 37° C. Additionally, during the flow experiment, the fluidic unit containing the test liquid was disposed in an incubator whose chamber temperature was maintained at 37° C. as well.

Figures 17A, 17B, 17C, 17D, 17E:
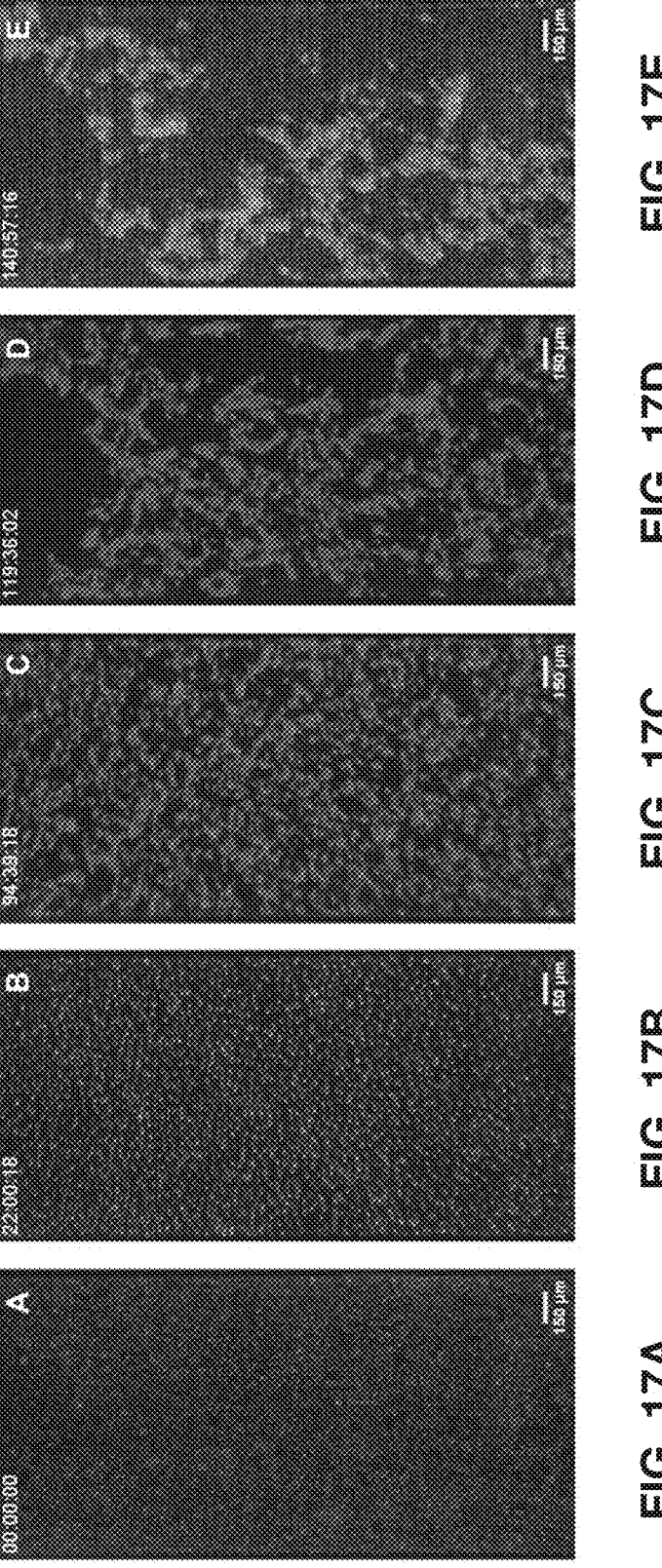
FIGS. 17A-17E are a sequence of fluorescent images taken during a dynamic assay in which A549 lung carcinoma epithelial cells (green) were cultured on a microfluidic chip (FIG. 17A) and activated T-cells (red) flowed over the A549 cells such that the T-cells bound to the A549 cells (FIG. 17B) and were recruited over time (FIG. 17C) to cause detachment of the A549 cells due to T-cell mediated killing (FIGS. 17D and 17E).

The flow was recorded using a monochromatic CMOS camera from Hamamatsu Photonics K.K. whose field of view was set to 512×512. The camera was arranged such that its image sensor received the fluorescent light from the stained A549 cells and T-cells during the flow experiment after the light passed through a microscope and a beam splitter that caused a first portion of the light (e.g., the green light) to strike a first part of the image sensor and a second portion of the light (e.g., the red light) to strike a second part of the image sensor. The portions of the video that included the captured green light and the portions of the video that included the captured red light were superimposed in ImageJ using a script to yield a processed video showing the T-cells (in red) flowing over and interacting with the A549 cells (in green). FIGS. 17A-17E show frames of the resulting video at the beginning of the flow experiment (FIG. 17A), 22 hours and 18 seconds into the flow experiment (FIG. 17B), 94 hours, 39 minutes, and 18 seconds into the flow experiment (FIG. 17C), 119 hours, 36 minutes, and 2 seconds into the flow experiment (FIG. 17D), and 140 hours, 57 minutes, and 16 seconds into the flow experiment (FIG. 17E). As shown, the A549 cells began attached to the channel (FIG. 17A), the T-cells bound to the A549 cells when flowing over them (FIG. 17B) and accumulated over time (FIG. 17C), and the A549 cells detached from the channel due to T-cell mediated killing (FIGS. 17D and 17E). The assay thus showed the effectiveness of the T-cells against the A549 lung carcinoma epithelial cells under flow conditions.

Example 2

Figure 18A:
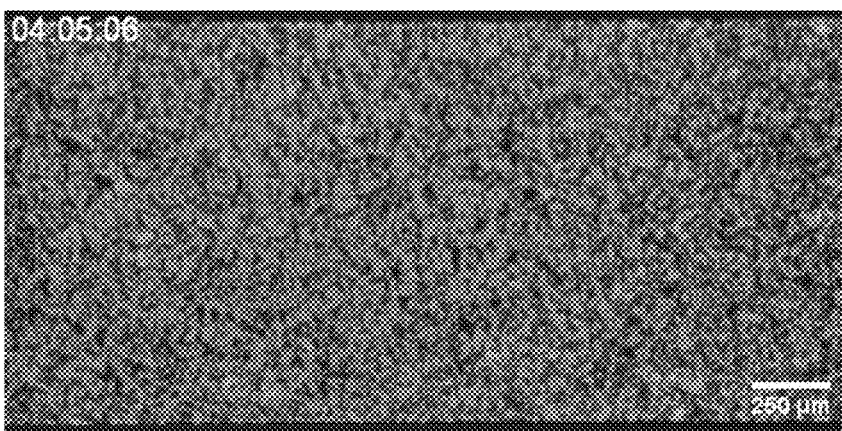
FIG. 18A is a fluorescent image of HeLa CD19+ cervical carcinoma cells (green) that were engineered to express CD19 and were cultured in a channel of a microfluidic chip.
Figure 18B:
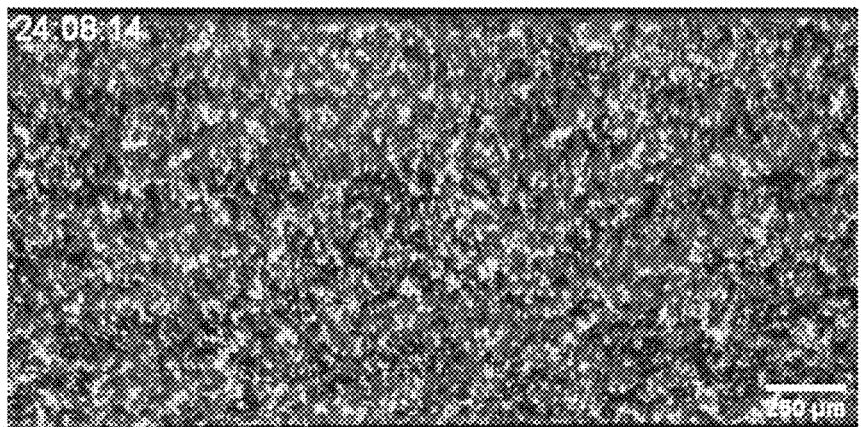
FIG. 18B is a fluorescent image of anti-CD19-ScFv-CD28-CD3ζ CAR-T cells (red) bound to HeLa CD19+ cervical cancer carcinoma cells (green) cultured in a channel of a microfluidic chip after the CAR-T cells flowed over the HeLa CD19+ cells for over 24 hours.
Figure 18C:
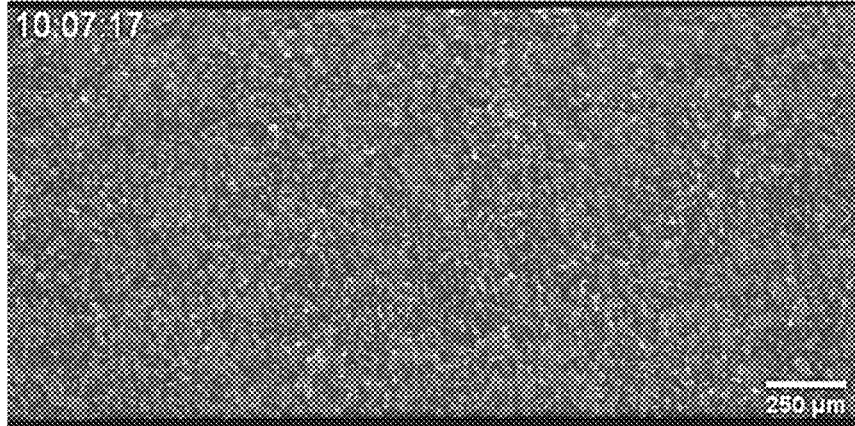
FIG. 18C is a fluorescent image of anti-CD19 CAR-NK cells (red) bound to HeLa CD19+ cervical cancer carcinoma cells (green) cultured in a channel of a microfluidic chip after the CAR-NK cells flowed over the HeLa CD19+ cells for over 10 hours.

Other flow-based assays with fluorescence microscopy were performed using the procedure of Example 1, except that the cultured target cells were HeLa CD19+ cervical cancer carcinoma cells marked with the Qtracker™ 525 (e.g., green) staining solution and the therapeutic reagent marked with the Qtracker™ 625 (e.g., red) staining solution was, in a first assay, anti-CD19-ScFv-CD28-CD3ζ CAR-T cells and, in a second assay, anti-CD19 CAR-NK cells. FIG. 18A is an image from a video of cultured and stained HeLa CD19+ cervical cancer carcinoma cells in the channel of an Ibidi® Luer μ-Slide. FIG. 18B is an image from a video of the flow experiment in the first assay 24 hours, 8 minutes, and 14 seconds into the flow experiment and shows binding and recruitment of the CD19-ScFv-CD28-CD3ζ CAR-T cells to the HeLa CD19+ cervical cancer carcinoma cells under flow conditions. FIG. 18C is an image from a video of the flow experiment in the second assay 10 hours, 7 minutes, and 17 seconds into the flow experiment and shows binding and recruitment of the anti-CD19 CAR-NK cells to the HeLa CD19+ cervical cancer carcinoma cells under flow conditions.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the products, systems, and methods are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of performing an assay, the method comprising:

culturing target cells in one or more channels of one or more microfluidic chips such that the cultured target cells are disposed in the channel(s), each of the channel(s) having a volume that is less than or equal to 100 microliters (µL) and the cultured target cells comprising a first fluorescent agent having an emission spectrum that comprises a first peak wavelength; and for each of one or more test liquids that each comprise a therapeutic reagent that comprises a second fluorescent agent having an emission spectrum that comprises a second peak wavelength that is at least 10% different than the first peak wavelength:

flowing the test liquid over the cultured target cells that are disposed in at least one of the channel(s); and while flowing the test liquid over the cultured target cells, capturing one or more sequences of images, wherein each of the sequence(s) of images is:

of an area containing at least a portion of at least one of the channel(s) in which the cultured target cells are disposed and over which the test liquid flows; and captured with a respective one of one or more cameras;

wherein for each of the sequence(s) of images, capturing the sequence of images comprises receiving light emitted by the first and second fluorescent agents at an image sensor of the camera that captures the sequence of images, wherein:

a first portion of the light emitted by the first and second fluorescent agents is directed to a first part of the image sensor of the camera, wherein the first portion of the light:

includes the first peak wavelength; and does not include the second peak wavelength; and a second portion of the light emitted by the first and second fluorescent agents is directed to a second part of the image sensor of the camera, wherein the second portion of the light:

includes the second peak wavelength; and does not include the first peak wavelength.

2. The method of claim 1, wherein each of the camera(s) is a monochrome camera.

3. The method of claim 1, comprising, for each of the sequence(s) of images, processing the captured sequence of images at least by, for each of the images of the sequence, superimposing a first portion of the image captured by the first part of the image sensor and a second portion of the image captured by the second part of the image sensor.

4. The method of claim 1, wherein for each of the test liquid(s), for each of the sequence(s) of images, the camera captures at least 70 images of the sequence per second during at least a portion of a period over which the test liquid flows over the cultured target cells.

5. The method of claim 1, comprising, for each of the test liquid(s):

while flowing the test liquid over the cultured target cells, heating the cultured target cells over which the test liquid flows;

wherein the microfluidic chip(s) comprising the channel(s) in which the test liquid flows are disposed in an incubator chamber while heating the cultured target cells and capturing the sequence(s) of images.

6. The method of claim 5, comprising, for each of the test liquid(s), directing carbon dioxide ($CO_2$) from a $CO_2$ source, oxygen ($O_2$) from an $O_2$ source, nitrogen ($N_2$) from an $N_2$ source, and/or air from an air source in which a pressure of the air is higher than ambient pressure into the incubator chamber while the microfluidic chip(s) comprising the channel(s) in which the test liquid flows are disposed in the incubator chamber and while flowing the test liquid over the cultured target cells.

7. The method of claim 5, comprising, for each of the test liquid(s), directing moisture into the incubator chamber while the microfluidic chip(s) comprising the channel(s) in which the test liquid flows are disposed in the incubator chamber and while flowing the test liquid over the cultured target cells.

8. The method of claim 1, wherein for each of the test liquid(s), flowing the test liquid over the cultured target cells in at least one of the channel(s) is performed such that, for each of the channel(s), a shear stress between the test liquid and a surface in the channel is between 1 and 100 dynes per square centimeter ($dyn/cm^2$).

9. The method of claim 1, wherein the target cells comprise cancer cells.

10. The method of claim 1, wherein the therapeutic reagent comprises lymphocytes.

11. The method of claim 1, wherein for each of the test liquid(s), flowing the test liquid over the cultured target cells is performed for at least 1 day.

12. The method of claim 1, wherein the volume of each of the channel(s) is less than or equal to 50 µL.

13. The method of claim 1, wherein:

the one or more channels of the one or more microfluidic chips comprise two or more channels;

the target cells include two or more types of target cells; and culturing the target cells comprises culturing each type of the target cells in a respective one of the channels.

14. The method of claim 13, wherein for each of the test liquid(s), flowing the test liquid over the target cells is performed such that the test liquid flows successively through at least two of the channels.

15. The method of claim 1, wherein:

the target cells are from a patient; and the method comprises determining, for each of the test liquid(s) and based at least in part on the captured sequence(s) of images, whether to administer the therapeutic reagent of the test liquid to the patient.

16. The method of claim 1, wherein:

the one or more channels of the one or more microfluidic chips comprise two or more channels;

the one or more test liquids comprise two or more test liquids, wherein for each of the test liquids:

the therapeutic reagent of the test liquid is different than the therapeutic reagent of each other of the test liquids; and the channel(s) through which the test liquid flows are different than the channel(s) through which each other of the test liquids flow.

17. The method of claim 1, comprising determining, for each of the test liquid(s) and based at least in part on the captured sequence(s) of images:

an extent to which the therapeutic reagent of the test liquid kills the target cells over which the test liquid flows; and/or an extent to which the therapeutic reagent of the test liquid binds to the target cells over which the test liquid flows.

\* \* \* \* \*